(12) United States Patent
Jalgaonkar et al.

(10) Patent No.: US 11,666,731 B2
(45) Date of Patent: **\*Jun. 6, 2023**

(54) CATHETER INCLUDING AN INNER LINER WITH A FLEXIBLE DISTAL SECTION

(71) Applicant: Covidien LP, Mansfield, MA (US)

(72) Inventors: Ujwal Jalgaonkar, Irvine, CA (US); Edwin Wang, Tustin, CA (US); David P. Marchesiello, Laguna Niguel, CA (US)

(73) Assignee: Covidien LP, Mansfield, MA (US)

( \* ) Notice: Subject to any disclaimer, the term of this patent is extended or adjusted under 35 U.S.C. 154(b) by 519 days.

This patent is subject to a terminal disclaimer.

(21) Appl. No.: 16/730,350

(22) Filed: Dec. 30, 2019

(65) Prior Publication Data
US 2020/0129733 A1    Apr. 30, 2020

Related U.S. Application Data

(63) Continuation of application No. 15/492,337, filed on Apr. 20, 2017, now Pat. No. 10,537,710.

(51) Int. Cl.
*A61M 25/00* (2006.01)
*A61B 17/22* (2006.01)

(52) U.S. Cl.
CPC .... *A61M 25/0051* (2013.01); *A61M 25/0052* (2013.01); *A61M 25/0053* (2013.01);
(Continued)

(58) Field of Classification Search
CPC .......... A61M 25/0051–0054; A61M 25/0045; A61M 25/0012; A61M 25/0013;
(Continued)

(56) References Cited

U.S. PATENT DOCUMENTS

| 3,621,848 | A | | 11/1971 | Magovern |
| 4,276,874 | A | \* | 7/1981 | Wolvek ............. A61M 25/1038 |
| | | | | 604/914 |

(Continued)

FOREIGN PATENT DOCUMENTS

| CN | 1473057 A | 2/2004 |
| CN | 102188236 A | 9/2011 |

(Continued)

OTHER PUBLICATIONS

Biotechnology Companies; Patent Application Titled "Steerable Catheter Having Intermediate Stiffness Transition Zone" Published Online, Biotech BusinessWeek, NewsRx LLC, Sep. 22, 2014, 5 pp.

(Continued)

*Primary Examiner* — Theodore J Stigell
(74) *Attorney, Agent, or Firm* — Shumaker & Sieffert, P.A.

(57) ABSTRACT

In some examples, a catheter includes a catheter body including an outer jacket and an inner liner. The inner liner may include a proximal section including a proximal end of the inner liner and a distal section including a distal end of the inner liner. The distal section may include an inner liner defining a plurality of cuts. Each cut may extend at least partially through the liner wall. The one or more cuts defined in the liner wall of the distal section of the inner liner may increase a bending flexibility of the distal section relative to the proximal section of the inner liner, while maintaining a suitable tensile strength of the distal section.

22 Claims, 8 Drawing Sheets

(52) U.S. Cl.
CPC ......... *A61M 25/0054* (2013.01); *A61B 17/22* (2013.01); *A61M 25/005* (2013.01); *A61M 25/0012* (2013.01); *A61M 25/0013* (2013.01); *A61M 25/0045* (2013.01); *A61M 2025/0047* (2013.01); *A61M 2210/12* (2013.01)

(58) Field of Classification Search
CPC ........ A61M 25/005; A61M 2025/0047; A61M 2025/105; A61B 17/22
See application file for complete search history.

(56) References Cited

U.S. PATENT DOCUMENTS

| | | |
|---|---|---|
| 4,354,491 A | 10/1982 | Marbry |
| 4,405,314 A | 9/1983 | Cope |
| 4,739,768 A | 4/1988 | Engelson |
| 4,753,222 A | 6/1988 | Morishita |
| 4,763,671 A | 8/1988 | Goffinet |
| 4,930,521 A | 6/1990 | Metzger et al. |
| 4,976,690 A | 12/1990 | Solar et al. |
| 5,007,901 A | 4/1991 | Shields |
| 5,308,342 A | 5/1994 | Sepetka et al. |
| 5,337,733 A | 8/1994 | Bauerfeind et al. |
| 5,358,493 A | 10/1994 | Schweich, Jr. et al. |
| 5,380,307 A | 1/1995 | Chee et al. |
| 5,423,773 A * | 6/1995 | Jimenez ............ A61M 25/0012 604/526 |
| 5,423,776 A | 6/1995 | Haindl |
| 5,437,632 A | 8/1995 | Engelson |
| 5,454,795 A | 10/1995 | Samson |
| 5,499,973 A | 3/1996 | Saab |
| 5,531,685 A | 7/1996 | Hemmer et al. |
| 5,599,326 A | 2/1997 | Carter |
| 5,649,909 A | 7/1997 | Cornelius |
| 5,755,704 A | 5/1998 | Lunn |
| 5,792,124 A | 8/1998 | Horrigan et al. |
| 5,830,227 A | 11/1998 | Fischell et al. |
| 5,833,604 A | 11/1998 | Houser et al. |
| 5,897,537 A * | 4/1999 | Berg ............... F16L 11/081 604/525 |
| 5,971,975 A | 10/1999 | Mills et al. |
| 5,984,907 A | 11/1999 | McGee et al. |
| 6,017,323 A * | 1/2000 | Chee ............... A61M 25/104 604/249 |
| 6,045,547 A | 4/2000 | Ren et al. |
| 6,143,013 A | 11/2000 | Samson et al. |
| 6,217,565 B1 | 4/2001 | Cohen |
| 6,319,244 B2 | 11/2001 | Suresh et al. |
| 6,436,112 B2 | 8/2002 | Wensel et al. |
| 6,582,536 B2 | 6/2003 | Shimada |
| 6,591,472 B1 | 7/2003 | Noone et al. |
| 6,648,874 B2 | 11/2003 | Parisi et al. |
| 6,841,214 B1 | 1/2005 | Keith et al. |
| 7,247,147 B2 | 7/2007 | Nishide et al. |
| 7,306,585 B2 | 12/2007 | Ross |
| 7,527,606 B2 | 5/2009 | Oepen |
| 7,625,337 B2 | 12/2009 | Campbell et al. |
| 7,658,723 B2 | 2/2010 | Von Oepen et al. |
| 7,914,467 B2 * | 3/2011 | Layman ............. A61M 25/09 600/585 |
| 8,105,246 B2 | 1/2012 | Voeller et al. |
| 8,142,413 B2 | 3/2012 | Root et al. |
| 8,241,245 B2 | 8/2012 | Markel et al. |
| 8,251,976 B2 | 8/2012 | Zhou |
| 8,282,677 B2 | 10/2012 | O'Connor et al. |
| 8,323,432 B2 | 12/2012 | Quint |
| 8,382,738 B2 | 2/2013 | Simpson et al. |
| 8,574,283 B1 | 11/2013 | Kamat |
| 8,608,754 B2 | 12/2013 | Wensel et al. |
| 8,652,193 B2 | 2/2014 | Dorn |
| 8,684,999 B2 | 4/2014 | Tegg et al. |
| 8,702,679 B2 | 4/2014 | Deckman et al. |
| 8,725,228 B2 | 5/2014 | Koblish et al. |
| 8,758,295 B2 | 6/2014 | Schaeffer |
| 8,911,424 B2 | 12/2014 | Weadock et al. |
| 8,926,560 B2 | 1/2015 | Dinh et al. |
| 9,119,936 B2 | 9/2015 | Itou et al. |
| 9,320,831 B2 | 4/2016 | Trapp |
| 9,352,116 B2 | 5/2016 | Guo et al. |
| 9,399,113 B2 | 7/2016 | Sandford et al. |
| 10,039,918 B2 | 8/2018 | Foster et al. |
| 10,537,710 B2 * | 1/2020 | Jalgaonkar ........ A61M 25/0052 |
| 2002/0156459 A1 | 10/2002 | Ye et al. |
| 2003/0135198 A1 | 7/2003 | Berhow et al. |
| 2004/0087933 A1 | 5/2004 | Lee et al. |
| 2006/0084939 A1 | 4/2006 | Lentz |
| 2006/0100571 A1 | 5/2006 | Venturelli |
| 2006/0106351 A1 | 5/2006 | Lareau |
| 2006/0189896 A1 * | 8/2006 | Davis ............... A61M 25/09 600/585 |
| 2006/0264905 A1 | 11/2006 | Eskridge et al. |
| 2007/0100285 A1 | 5/2007 | Griffin et al. |
| 2007/0233040 A1 | 10/2007 | Macnamara et al. |
| 2007/0276354 A1 | 11/2007 | Osborne |
| 2008/0048011 A1 | 2/2008 | Weller |
| 2008/0161761 A1 | 7/2008 | Tegg et al. |
| 2009/0030400 A1 | 1/2009 | Bose et al. |
| 2009/0160112 A1 | 6/2009 | Ostrovsky |
| 2009/0171318 A1 | 7/2009 | Drewes, Jr. |
| 2010/0049192 A1 | 2/2010 | Holtz et al. |
| 2011/0028940 A1 | 2/2011 | Lorenz |
| 2011/0238041 A1 | 9/2011 | Lim et al. |
| 2012/0041411 A1 | 2/2012 | Horton et al. |
| 2012/0101480 A1 | 4/2012 | Ingle et al. |
| 2012/0116350 A1 | 5/2012 | Strauss et al. |
| 2012/0172717 A1 | 7/2012 | Gonda |
| 2012/0245562 A1 | 9/2012 | Bihlmaier |
| 2012/0303051 A1 | 11/2012 | Matsuura |
| 2013/0172851 A1 | 7/2013 | Shimada et al. |
| 2013/0245610 A1 | 9/2013 | Haslinger et al. |
| 2013/0253417 A1 | 9/2013 | Dinh et al. |
| 2014/0046297 A1 | 2/2014 | Shimada et al. |
| 2014/0173878 A1 | 6/2014 | Merk et al. |
| 2014/0243963 A1 | 8/2014 | Sheps et al. |
| 2014/0277058 A1 | 9/2014 | Wu |
| 2015/0100043 A1 | 4/2015 | Govari et al. |
| 2015/0157827 A1 | 7/2015 | Glasel |
| 2015/0216692 A1 | 8/2015 | Shannon et al. |
| 2015/0231367 A1 | 8/2015 | Salstrom et al. |
| 2016/0346503 A1 | 12/2016 | Jackson et al. |
| 2016/0346506 A1 | 12/2016 | Jackson et al. |
| 2016/0346507 A1 | 12/2016 | Jackson et al. |
| 2016/0346508 A1 | 12/2016 | Williams et al. |
| 2017/0182291 A1 | 6/2017 | Griffin et al. |

FOREIGN PATENT DOCUMENTS

| | | |
|---|---|---|
| CN | 104797290 A | 7/2015 |
| EP | 0643979 A1 | 3/1995 |
| EP | 0718003 A1 | 6/1996 |
| EP | 0810003 A2 | 3/1997 |
| EP | 1340516 A1 | 9/2003 |
| EP | 2364746 A1 | 9/2011 |
| WO | 9305842 A1 | 4/1993 |
| WO | 2004033015 A1 | 4/2004 |
| WO | 2010068793 A1 | 6/2010 |
| WO | 2013185148 A1 | 12/2013 |

OTHER PUBLICATIONS

"Entellus Medical, Inc.; Patent Issued for Guide Catheter and Method of Use," Medical Devices & Surgical Technology Week, NewsRx, Mar. 16, 2014, 6 pp.

"Braided Catheter Shafts & Coiled Catheter Shafts," AdvancedCath, retrieved from http://advancedcathetermanufacturing.com/braided-and-coiled-catheter-shafts/on Jan. 19, 2015, 2 pp.

"Braid-Reinforced Shafts," Vention Medical, retrieved from http://www.ventionmedical.com/products-and-services/braid-reinforced-shafts/ on Jan. 19, 2015, 2 pp.

(56) References Cited

OTHER PUBLICATIONS

"C-Flex™ Ureteral Catheters," Boston Scientific, retrieved from http://www.bostonscientific.com/en-US/products/catheters-ureteral/c-flex.html on Jan. 15, 2015, 3 pp.
"Marathon™ Flow Directed Micro Catheters," Covidien, retrieved from http://www.ev3.net/neuro/US/micro-catheters/marathontrade-flow-directed-catheter.htm on Jan. 19, 2015, 2 pp.
"Microcatheters: Valet® Microcatheter," Volcano Corporation, retrieved from http://www.volcanocorp.com/products/valet.php#.VddxLflVhvB on Jan. 15, 2015, 2 pp.
"Putnam Plastics New Taper-TIE™ Technology Optimizes Variable Flexibility of Medical Catheter Shafts," Dec. 18, 2012, 1 pp.
"SIDEKICK® Support Catheter, Enhanced CROSSER® Catheter Deliverability," Bard Peripheral Vascular, 2013, (Applicant points out, in accordance with MPEP 609.04(a), that the year of publication, 2013, is sufficiently earlier than the effective U.S. filing date, so that the particular month of publication is not in issue.) 2 pp.
Hartford, "New Extrusion Techniques Advance Catheter Design," Medical Device and Diagnostic Industry, Feb. 20, 2013, 4 pp.
International Search Report and Written Opinion of International Application No. PCT/US2018/028370, dated Jul. 3, 2018, 18 pp.
International Preliminary Report on Patentability from International Application No. PCTUS2018/028370, dated Oct. 31, 2019, 11 pp.
Prosecution History from U.S. Appl. No. 15/492,337, dated May 14, 2018 through Dec. 23, 2019, 120 pp.
Response to Communication pursuant to Rules 161(1) and 162 EPC dated Nov. 27, 2019, from counterpart European Application No. 18723182.4, filed May 18, 2020, 17 pp.
First Office Action and Search Report, and machine translation thereof, from counterpart Chinese Application No. 201880025832.5, dated May 8, 2021, 16 pp.

* cited by examiner

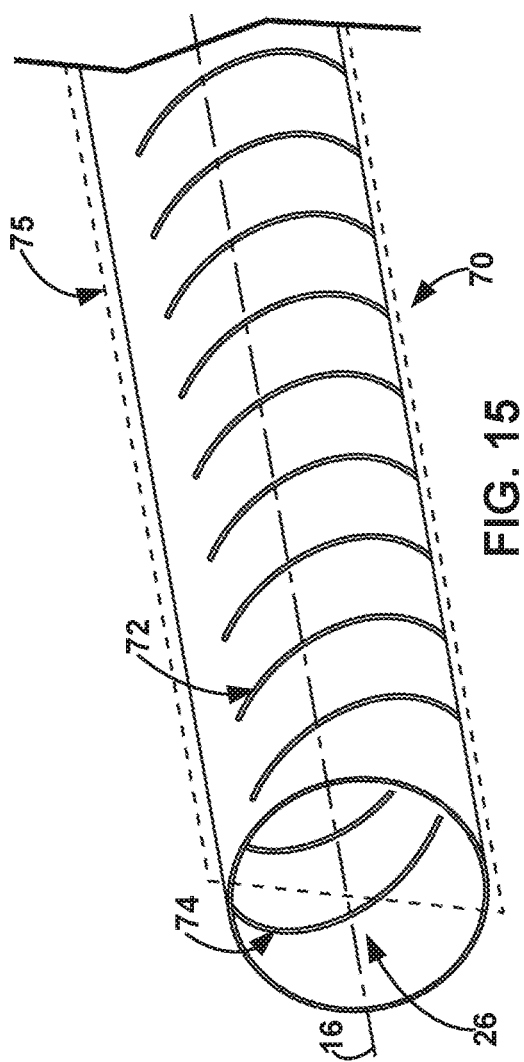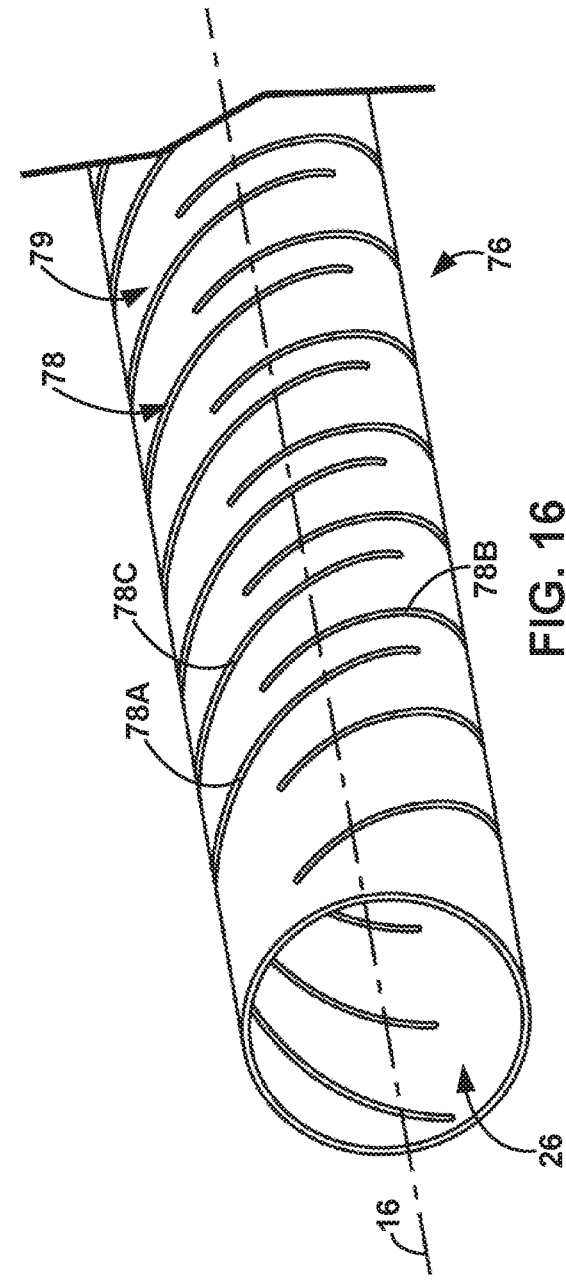

CATHETER INCLUDING AN INNER LINER WITH A FLEXIBLE DISTAL SECTION

This application is a continuation of U.S. patent application Ser. No. 15/492,337, filed Apr. 20, 2017, and entitled, "CATHETER INCLUDING AN INNER LINER WITH A FLEXIBLE DISTAL SECTION," the entire content of which is herein incorporated by reference.

TECHNICAL FIELD

This disclosure relates to a medical catheter.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels.

SUMMARY

In some examples, a catheter includes an inner liner comprising a proximal section and a distal section, the distal section including a liner wall defining one or more cuts. The one or more cuts extend at least partially through a thickness of the inner wall. The catheter may also include one or more other elements, such as, but not limited to, an outer jacket and a support member (e.g., a coil and/or a braid). The one or more cuts defined in the liner wall of the distal section of the inner liner may increase a bending flexibility of the distal section relative to the proximal section of the inner liner, while maintaining a suitable tensile strength of the distal section. This disclosure also describes examples of methods of forming the catheters described herein and methods of using the catheters.

Clause 1: In one example, a catheter includes an elongated body including an outer jacket and an inner liner, the inner lining extending between a proximal end and a distal end, and the inner liner defining a lumen, wherein the inner liner includes a proximal section including the proximal end and a distal section including the distal end. The distal section of the inner liner includes a liner wall defining a plurality of cuts, each cut extending at least partially through the liner wall.

Clause 2: In some examples of the catheter of clause 1, the lumen defined by the inner liner is an inner lumen of the elongated body.

Clause 3: In some examples of the catheter of clause 1 or 2, at least one cut of the plurality of cuts is a through-cut that extends through a thickness of the liner wall to the lumen.

Clause 4: In some examples of the catheter of any of clauses 1-3, at least one cut of the plurality of cuts is a partial cut, wherein the partial cut extends only partially through a thickness of the liner wall.

Clause 5: In some examples of the catheter of clause 4, the at least one cut extends from an outer surface of the liner wall and radially inward towards the lumen.

Clause 6: In some examples of the catheter of clause 4 or 5, the at least one cut extends through about 20% to about 80% of the thickness of the liner wall.

Clause 7: In some examples of the catheter of clause 6, the at least one cut extends through about 50% of the thickness of the liner wall.

Clause 8: In some examples of the catheter of any of clauses 1-7, at least one cut of the plurality of cuts is disposed in an arc around an outer surface of the inner liner.

Clause 9: In some examples of the catheter of any of clauses 1-8, at least one cut of the plurality of cuts is elongated in a direction substantially perpendicular to a longitudinal axis of the inner liner.

Clause 10: In some examples of the catheter of any of clauses 1-9, at least one cut of the plurality of cuts is oblong shaped, a major axis of the oblong shape extending in a direction substantially perpendicular to a longitudinal axis of the inner liner.

Clause 11: In some examples of the catheter of any of clauses 1-10, each cut is elongated in a direction that define an angle from about 45 degrees to about 90 degrees relative to a longitudinal axis of the inner liner.

Clause 12: In some examples of the catheter of any of clauses 1-11, at least one cut of the plurality of cuts is elongated in a direction substantially parallel to a longitudinal axis of the inner liner.

Clause 13: In some examples of the catheter of any of clauses 1-12, the inner liner has a circular cross-section, and at least one cut of the plurality of cuts extends around only part of a circumference of the circular cross-section.

Clause 14: In some examples of the catheter of clause 13, the at least one cut extends around less than 180 degrees of the circumference.

Clause 15: In some examples of the catheter of any of clauses 1-14, the at least one cut extends around less than 90 degrees of the circumference.

Clause 16: In some examples of the catheter of any of clauses 1-15, a density of the plurality of cuts decreases in a proximal direction, wherein the density corresponds to a number of cuts per unit length of the inner liner.

Clause 17: In some examples of the catheter of any of clauses 1-16, the cuts are symmetrically arranged relative to a longitudinal axis of the inner liner.

Clause 18: In some examples of the catheter of any of clauses 1-16, the cuts are asymmetrically arranged relative to a longitudinal axis of the inner liner.

Clause 19: In some examples of the catheter of any of clauses 1-18, the plurality of cuts do not overlap with one another in a direction along a longitudinal axis of the inner liner.

Clause 20: In some examples of the catheter of any of clauses 1-19, at least one cut of the plurality of cuts overlaps with another cut in a direction along a longitudinal axis of the inner liner.

Clause 21: In some examples of the catheter of any of clauses 1-20, the plurality of cuts form a pattern along the distal section, the pattern including two cuts that include medial sections which are adjacent to each other, wherein at least one end of each of the two cuts are displaced by a third cut.

Clause 22: In some examples of the catheter of any of clauses 1-21, the plurality of cuts form a pattern along the distal section, wherein the liner includes first and second sides of a median plane extending along a longitudinal axis of the inner liner, and wherein the pattern includes a first set of the plurality of cuts on the first side, and a second set of the plurality of cuts on the second side, wherein the first and second sets mirror each other.

Clause 23: In some examples of the catheter of any of clauses 1-22, a distal-most cut of the plurality of cuts is arranged between about 0.02 centimeters and about 30 centimeters from the distal end of the inner liner.

Clause 24: In some examples of the catheter of clauses 23, a proximal-most cut of the plurality of cuts is about 5 centimeters to about 35 centimeters from the distal end of the inner liner.

Clause 25: In some examples of the catheter of any of clauses 1-24, the distal section of the inner liner has a length of about 10 centimeters to about 30 centimeters.

Clause 26: In some examples of the catheter of clause 25, the distal section of the inner liner has a length of about 5 centimeters to about 10 centimeters.

Clause 27: In some examples of the catheter of any of clauses 1-26, a length of the distal section is smaller than a length of the proximal section, the length being measured in a direction parallel to a longitudinal axis of the inner liner.

Clause 28: In some examples of the catheter of any of clauses 1-27, a thickness of the distal section of the liner wall decreases toward the distal end.

Clause 29: In some examples of the catheter of any of clauses 1-27, a thickness of the liner wall is substantially uniform between the proximal end and the distal end.

Clause 30: In some examples of the catheter of any of clauses 1-29, the inner liner is more lubricious than the outer jacket.

Clause 31: In some examples of the catheter of any of clauses 1-30, an inner surface of the liner wall is smooth.

Clause 32: In some examples of the catheter of any of clauses 1-31, the inner liner comprises a polymer material.

Clause 33: In some examples of the catheter of clause 32, the polymer material includes one or more of: polytetrafluoroethylene or polyimide.

Clause 34: In some examples of the catheter of clause 32 or 33, the polymer material includes expanded polytetrafluoroethylene.

Clause 35: In some examples of the catheter of any of clauses 1-34, the inner liner comprises a unitary liner including the distal section and the proximal section.

Clause 36: In some examples, a catheter includes an elongated body comprising an outer jacket; and an inner liner extending between a proximal end and a distal end, the inner liner defining a lumen, wherein the inner liner includes a proximal section including the proximal end and a distal section including the distal end, and wherein the distal section of the inner liner includes a liner wall defines a helical cut.

Clause 37: In some examples of the catheter of clause 36, the lumen defined by the inner liner is an inner lumen of the elongated body.

Clause 38: In some examples of the catheter of clause 36 or 37, the helical cut is a through-cut that extends through a thickness of the liner wall to the lumen.

Clause 39: In some examples of the catheter of any of clauses 36-38, the helical cut is a partial cut extending only partially through a thickness of the liner wall.

Clause 40: In some examples of the catheter of clause 39, the helical cut extends from an outer surface of the liner wall and radially inward towards the lumen.

Clause 41: In some examples of the catheter of clause 39 or 40, the helical cut extends through about 20% to about 80% of the thickness of the liner wall.

Clause 42: In some examples of the catheter of any of clauses 36-41, the helical cut defines a helix having a pitch of about 1 millimeter to 5 millimeters between adjacent turns of the cut.

Clause 43: In some examples of the catheter of any of clauses 36-42, a proximal end of the helical cut is about 5 centimeters to about 35 centimeters from the distal end of the inner liner.

Clause 44: In some examples of the catheter of any of clauses 36-43, the distal section of the inner liner has a length of about 10 centimeters to about 35 centimeters.

Clause 45: In some examples of the catheter of any of clauses 36-44, a thickness of the distal section of the liner wall decreases toward the distal end.

Clause 46: In some examples of the catheter of any of clauses 36-45, an inner surface of the liner wall is smooth.

Clause 47: In some examples of the catheter of any of clauses 36-46, the inner liner comprises a unitary liner including the distal section and the proximal section.

Clause 48: In some examples, a method comprises forming an inner liner, the inner liner extending between a proximal end and a distal end, and defining a lumen, wherein the inner liner includes a proximal section including the proximal end and a distal section including the distal end, and wherein the distal section of the inner liner includes a liner wall defining a plurality of cuts, each cut extending at least partially through the liner wall; and positioning an outer jacket over an inner liner.

Clause 49: In some examples of the method of clause 48, forming the inner liner comprises cutting the plurality of cuts in the liner wall of the distal section of the inner liner.

Clause 50: In some examples of the method of clause 49, cutting the plurality of cuts in the liner wall comprises defining the plurality of cuts with a laser cutter.

Clause 51: In some examples of the method of any of clauses 48-50, forming the inner liner includes ram extruding a polytetrafluoroethylene material.

Clause 52: In some examples of the method of any of clauses 48-51, forming the inner liner comprises depositing a material of the inner liner over a mask, the mask defining the plurality of cuts.

Clause 53: In some examples of the method of clause 52, depositing the material of the inner liner includes spraying the material onto the inner liner over the mask.

Clause 54: In some examples of the method of any of clauses 48-51, forming the inner liner comprises printing the inner liner using a three-dimensional printer.

Clause 55: In some examples of the method of any of clauses 48-54, forming the inner liner comprises: defining the plurality of cuts in a tubular body defining the lumen; and, subsequently, stretching the tubular body along a longitudinal axis of the tubular body.

Clause 56: In some examples a method comprises introducing a guide member into vasculature of a patient; and introducing a catheter in the patient over the guide member, the catheter including an elongated body comprising: an outer jacket; and an inner liner extending between a proximal end and a distal end, the inner liner defining a lumen, wherein the inner liner includes a proximal section including the proximal end and a distal section including the distal end, wherein the distal section of the inner liner includes a liner wall defining a plurality of cuts, each cut extending at least partially through the liner wall.

Clause 57: In some examples of the method of clause 56, the method further comprises introducing a medical device into the lumen of the inner liner.

Clause 58: In some examples of the method of clause 56 or 57, the method further comprises aspirating thrombus through an inner lumen of the catheter.

Clause 59: In some examples of the method of any of clauses 56-58, the method further comprises advancing a distal end of the catheter into an intracranial blood vessel.

Clause 60: In some examples of the method of clause 59, the method further comprises removing thrombus from the intracranial blood vessel with the catheter.

Clause 61: In some examples of the method of clause 60, removing thrombus from the intracranial blood vessel with the catheter comprises aspirating the thrombus.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

FIG. 15 is a perspective view of a distal section of another example inner liner of a catheter body.

FIG. 16 is a perspective view of a distal section of another example inner liner of a catheter body.

DETAILED DESCRIPTION

Figure 1:
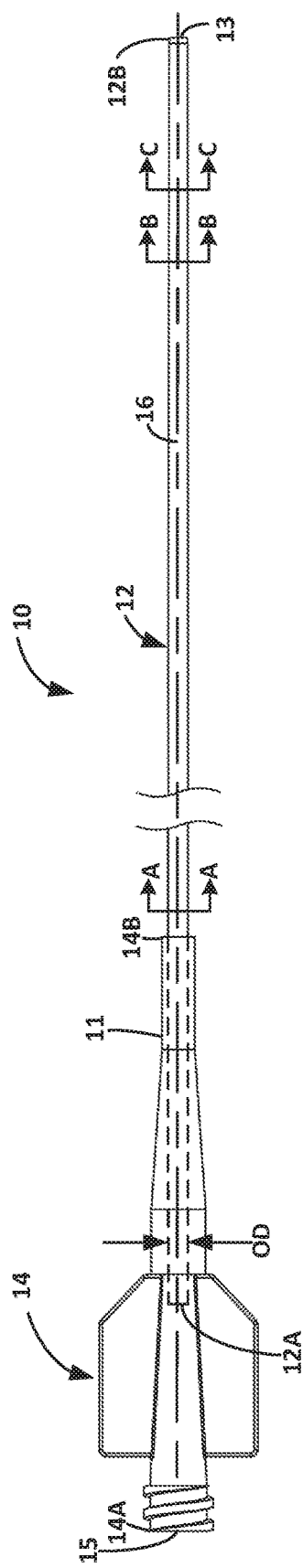
FIG. 1 is a side elevation view of an example catheter, which includes a catheter body and a hub.

In some examples, a medical catheter ("catheter") described herein includes a relatively flexible catheter body that is configured to be navigated through vasculature of a patient, e.g., tortuous vasculature in a brain of the patient. The catheter body includes a relatively flexible distal section that may exhibit increased flexibility relative to a proximal portion of the catheter body. In some examples, the catheter body includes an inner liner and an outer jacket, and the increased flexibility of the distal section may be at least partially (e.g., partially or fully) attributable to the configuration of the inner liner. For example, a distal section of the inner liner may define one or more cuts, which helps to increase a bending flexibility of the distal section of the inner liner while maintaining a desirable tensile strength of the inner liner. The one or more cuts may have any suitable configuration that helps to increase the bending flexibility of the inner liner while maintaining a desirable tensile strength of the inner liner and the overall catheter body. For example, the one or more cuts may be an absence of material in or a locally thinner portion of the liner wall (e.g., a groove, divot, pocket, through-hole, or the like in an otherwise continuous surface), or may be an incision in a liner wall of the inner liner that is formed without removing material from the liner wall.

A desirable tensile strength of the inner liner or catheter body can be, for example, a minimum tensile strength for a particular use of the catheter. Inadequate tensile strength of an inner liner or a catheter body (of which the inner liner is part) can translate into poor navigability of the catheter body through vasculature of a patient when a clinician is advancing and retracting the catheter body in tortuous anatomy. For example, if a distal tensile strength of the inner liner or catheter body is too low, then the distal end of the catheter may not retract from the patient at the same rate as the proximal portion of the catheter, which may reduce the control over the catheter perceived by the clinician. In addition, if the tensile strength of the inner liner (and, as a result, the catheter body) is too low, then the distal end of the catheter may remain in place while the proximal end stretches away from it, which may cause a distal portion of the catheter body to break away from the rest of the catheter body.

The tensile strength and flexibility provided by the arrangement of the one or more cuts in an inner liner described herein may translate into better navigability when a clinician is advancing or retracting the catheter, such as in tortuous anatomy. For example, the tensile strength of the inner liners defining one or more cuts described herein may be sufficiently high enough to enable the distal section of the inner liner to be retracted from a patient without compromising the structural integrity of the catheter body. Further, the tensile strength of the inner liners described herein may enable both the distal end and the proximal portion of a catheter body including one of the inner liners to be retracted from the vessel of a patient at the same rate, which may provide the clinician with a perception of more control over the catheter.

By using the devices and techniques herein, the tensile strength of the inner liner may be sufficiently strong enough such that distal section of the inner liner is capable of retracting safely, even if, for example, the vessel around the distal end of the catheter is constricting the catheter.

An inner liner may include a liner wall that defines an inner lumen and an outer surface of the inner liner. Each cut in the inner liner may extend at least partially through the liner wall, e.g., at least partially through a thickness of the liner wall or all the way through a thickness of the inner wall so as to expose an inner lumen of the inner liner. The thickness of the liner wall may be measured in a direction orthogonal to the longitudinal axis of the inner liner. In some examples, the liner wall may be thinner at a cut, which may allow for more flexibility of the inner liner at the region including and adjacent to the cut.

In some examples in which the one or more cuts extend only partially through a thickness of a liner wall of an inner liner, also referred to herein as partial cuts, the partial cuts may be defined by an outer surface of the liner wall. For example, the partial cuts may extend from the outer surface of the liner wall towards the inner lumen, but may not extend all the way through the liner wall to the inner lumen of the inner liner. By positioning the partial cuts on an outer surface of the liner wall, an inner surface of the inner liner may remain substantially smooth (e.g., smooth or nearly smooth, or without projections or indentations that would inhibit the passage of a medical device), which may facilitate passage of one or more medical devices (e.g., guide members, an embolic protection device or an embolic retrieval device, and the like) through the inner lumen of the inner liner. In other examples, however, the partial cuts may be defined by an inner surface of the liner wall in addition to, or instead of, the outer surface.

The one or more cuts defined by a distal section of an inner liner may be arranged in any suitable pattern on the distal section of the inner liner to provide the increased flexibility of the distal section, relative to an inner liner section that is similar to the distal section, but does not include the cuts. Example patterns formed by the one or more cuts are discussed in further detail below with reference to FIGS. 1-18.

In some examples in which the one or more cuts extend fully through a thickness of a liner wall of an inner liner, also referred to herein as through-cuts, the one or more cuts may be arranged so as not to divide the inner liner into physically separate portions.

An inner liner of a catheter body described herein includes a distal section including the one or more cuts, and a proximal section. For example, the inner liner may consist essentially of the proximal and distal sections. As an example, the distal section may be immediately adjacent to and mechanically connected to the proximal section (e.g., formed integrally with the proximal section or formed separate from the proximal section and attached thereto).

In some examples, a catheter including the inner liner comprising a distal section defining one or more cuts may be a variable stiffness catheter that increases in flexibility towards a distal end of the catheter. For example, a proximal section of the inner liner may not include any cuts or may have an arrangement of cuts (e.g., fewer cuts or a different pattern) different from that of the distal section, such that the distal section is more flexible than the proximal section. In this way, the cuts defined in the distal section of the inner liner may configure the distal section to be more flexible than a more proximal section of the inner liner. The variable stiffness catheter body may allow the catheter body to exhibit a relatively high level of pushability due to the stiffer proximal section of the inner liner which contributes to the overall stiffness of the catheter body, and exhibit a relatively high level of flexibility at the distal portion of the catheter body due at least in part to the configuration of the distal section of the inner liner.

In some examples, a catheter body of a catheter described herein includes an inner liner, a support element (e.g., a coil member or a braided member, or combinations thereof), and an outer jacket, which can interact to provide a relatively flexible elongated body of the catheter with sufficient structural integrity (e.g., column strength, which may be a measure of a maximum compressive load that can be applied to the catheter body without taking a permanent set) to permit the catheter body to be advanced through the vasculature via a pushing force applied to a proximal portion of the catheter body, e.g. without buckling, kinking, or otherwise undesirably deforming (e.g., ovalization). A distal portion of the catheter body may lead the catheter body through vasculature of a patient. The example inner liners described herein may increase the flexibility of the distal portion of the catheter body, and, therefore, may increase the navigability of the catheter body through vasculature compared to a catheter including an inner liner that is otherwise the same, but does not include the one or more cuts in a distal section.

Some catheters include catheter bodies that comprise an inner liner formed from polytetrafluoroethylene (PTFE), which may provide the catheter body with a lubricious inner surface and allow relatively easy delivery of interventional devices through the catheter body or relatively easy tracking of the catheter body over a guide member (e.g., a guidewire or a microcatheter). In some cases, a PTFE inner liner may impart stiffness to the overall catheter body that may make the catheter body less flexible and, therefore, less navigable through the vasculature, e.g., through the neurovasculature. While configuring an inner liner to include a distal section formed from a different, softer, or more flexible material than a proximal section of the inner liner may help provide a more flexible catheter body distal section, the softer or more flexible inner liner material may make the catheter body more prone to stretching and accordioning (e.g., the forming of multiple folds along a length of the inner liner and/or outer jacket). As an example, the proximal section of the inner liner may be formed from PTFE and the distal section may be formed from a non-PTFE material that is softer and more flexible than PTFE. The non-PTFE inner liner material may trade-off lubricity, column strength, and/or tensile strength for higher flexibility. In addition, due to the lower lubricity of non-PTFE inner liner materials compared to a PTFE inner liner, the non-PTFE inner liner may be less compatible with stentrievers or other medical devices that may be introduced to a treatment site through an inner lumen of the inner liner due to the relative frictional forces between the medical device and the inner liner, or other mechanical interactions between the medical device and the inner liner during delivery and retrieval of these devices through the catheter body.

The example inner liners described herein that include one or more cuts in a distal section may increase the flexibility of the catheter body, and, therefore, may increase the navigability of the catheter body through vasculature compared to a catheter including an inner liner that is otherwise the same, but does not include the one or more cuts in a distal section. The inner liner configurations described herein may allow a catheter body to include a PTFE inner liner without the stiffness limitations that may otherwise be associated with the PTFE inner liner. The inner liners described herein may be formed from any suitable material in addition to or instead of PTFE.

In some examples, a catheter body may include an inner liner formed from PTFE for a full length of the inner liner (from a proximal end to a distal end of the inner liner), and a distal section of the inner liner may include one or more cuts in the inner liner. In this way, the catheter body may exhibit the desired lubricity provided by PTFE, which may provide better compatibility with stentrievers or other medical devices that may be introduced in the inner lumen of the inner liner, and a more flexible distal section, while maintaining stiffness at a proximal section of the inner liner. The relatively higher degree of stiffness of the proximal section of the inner liner may help define a catheter body that has a desired level of pushability (e.g., transmission of pushing forces applied to a proximal portion of the catheter body to the distal portion of the catheter body). The relatively flexible distal section may facilitate navigation of the catheter body through vasculature of a patient by increasing the flexibility of the distal most portion of the catheter body, such that the catheter body may better traverse through tortuous vasculature while still maintaining a relatively high level of proximal pushability.

The catheter bodies described herein can be configured to exhibit a relatively high level of flexibility, pushability, torqueability, and/or structural integrity. In some examples, a catheter body includes an inner liner including a distal section defining one or more cuts, a structural support member, and an outer jacket, which interact to provide a flexible catheter body with sufficient structural integrity (e.g., column strength) to permit the catheter body to be advanced through the vasculature from a pushing force applied to a proximal portion of the catheter body, without buckling or undesirable bending (e.g., kinking) of the catheter body. In some examples, the flexible catheter body is configured to substantially conform to the curvature of the vasculature. In addition, in some examples, the catheter body has a column strength and flexibility that allow at least a distal portion of the catheter body to be navigated from a femoral artery, through the aorta of the patient, and into the intracranial vascular system of the patient, e.g., to reach a relatively distal treatment site, including the middle cerebral artery (MCA), internal carotid artery (ICA), the Circle of Willis, and tissue sites more distal than the MCA, ICA, and the Circle of Willis. The MCA and, consequently, vasculature distal to the MCA may be relatively difficult to access due to the carotid siphon anatomy that must be traversed to reach such locations.

In some examples, the catheter may be a guide catheter that acts as a conduit to help support a microcatheter. In other examples, the catheter may be a microcatheter. In either example, the catheter body of the catheter may define an inner lumen, which may be configured to receive one or more medical devices, deliver a therapeutic agent to a distal tissue site (e.g., a distal vascular site), remove thrombus (e.g., by aspiration) from the patient's vasculature, and the like or any combination thereof. Examples of therapeutic agents include, but are not limited to, an oxygenated medium or a pharmaceutical agent, which may be, for example, a vasodilator such as nifedipine or sodium nitroprusside, or a tissue plasminogen activator (t-PA), which can be used to breakdown blood clots.

In examples in which the inner lumen defined by the catheter body is used to remove thrombus from vasculature, the catheter may be referred to as an aspiration catheter. A vacuum may be applied to a proximal end of the catheter body to draw a thrombus into the inner lumen. An aspiration catheter may be used in a medical procedure to treat an ischemic insult, which may occur due to occlusion of a blood vessel that deprives brain tissue of oxygen-carrying blood. In some examples, in addition to being configured to be navigated to relatively distal tissue sites, an aspiration catheter may also include a distal tip configuration that is configured to substantially maintain its shape, even in the presence of the vacuum force applied to the catheter during the aspiration process.

The catheters described herein may be advanced to a target location within vasculature of the patient in cooperation with a guidewire, an inner catheter, or both, which may aid in the navigation (e.g., steering and manipulation) of the catheter through the vasculature. For example, an inner lumen of the catheter body may be configured to receive a guidewire or an inner catheter, such that the catheter body may be guided through vasculature over the guidewire or the inner catheter. A distal portion of an example catheter body described herein is configured to encourage navigability, due at least in part to the one or more cuts in the distal section of the inner liner.

Although primarily described as being used to reach relatively distal vasculature sites, the catheters described herein may readily be configured to be used with other target tissue sites. For example, the catheters may be used to access tissue sites throughout the coronary and peripheral vasculature, the gastrointestinal tract, the urethra, ureters, Fallopian tubes, and other body lumens.

Figure 2:
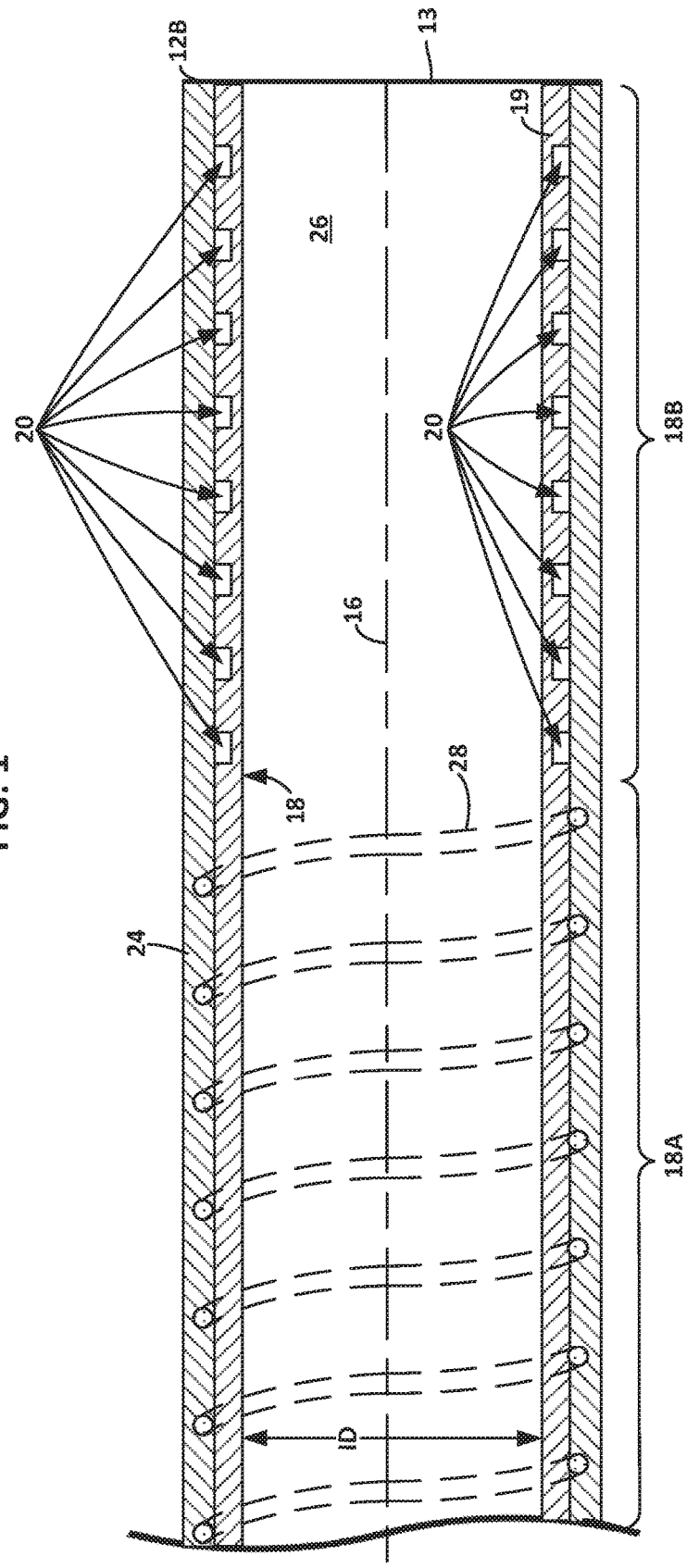
FIG. 2 is a conceptual cross-sectional view of a part of the catheter body of FIG. 1 including the distal end, where the cross-section is taken through a center of the catheter body and along a longitudinal axis of the catheter body.

FIG. 1 is a conceptual side elevation view of an example catheter 10, which includes catheter body 12 and hub 14. Catheter hub 14 is positioned at a proximal end of catheter 10 and defines an opening through which an inner lumen 26 (such as shown in FIG. 2) of catheter body 12 may be accessed and, in some examples, closed. For example, catheter hub 14 may include a luer connector for connecting to another device, a hemostasis valve, or another mechanism or combination of mechanisms. In some examples, catheter 10 includes strain relief member 11, which may be a part of hub 14 or may be separate from hub 14. In other examples, the proximal end of catheter 10 can include another structure in addition to, or instead of, hub 14.

Catheter body 12 is an elongated body that extends from proximal end 12A to distal end 12B and defines at least one inner lumen 26 (shown in FIG. 2). In some examples, catheter body 12 is elongated such that its length dimension (e.g., from proximal end 12A to distal end 12B is larger than an outer diameter dimension of catheter body 12. In some examples, the length dimension is at least 100 times larger than the outer diameter dimension. Catheter body 12 may have a single inner lumen 26, or multiple inner lumens (e.g., two inner lumens or three inner lumens). Inner lumen 26 may terminate at any suitable point along catheter body 12, which may depend on the procedure with which catheter 10 is to be used. For example, inner lumen 26 may terminate at distal opening 13 defined by catheter body 12 or may terminate at an opening defined along a side wall of catheter body 12. In some examples, an inner liner of catheter body 12 defines inner lumen 26. In other examples, however, another structure may be radially inward of inner lumen 26. Thus, although examples in which an inner liner of catheter body 12 defines inner lumen 26 are primarily described herein, in other examples, another structure may define inner lumen 26.

In the example shown in FIG. 1, proximal end 12A of catheter body 12 is received within hub 14 and is mechanically connected to hub 14 via an adhesive, welding, or another suitable technique or combination of techniques. Opening 15 defined by hub 14 and located at proximal end 14A of hub 14 is aligned with inner lumen 26 of catheter body 12, such that inner lumen 26 of catheter body 12 may be accessed via opening 15.

Catheter body 12 has a suitable length for accessing a target tissue site within the patient from a vascular access point. The length may be measured along longitudinal axis 16 of catheter body 12. The target tissue site may depend on the medical procedure for which catheter 10 is used. For example, if catheter 10 is a distal access catheter used to access vasculature in a brain of a patient from a femoral artery access point at the groin of the patient, catheter body 12 may have a length of about 125 centimeters (cm) to about 135 cm or more, such as about 132 cm, although other lengths may be used.

Catheter body 12 may be used to access relatively distal locations in a patient, such as the middle cerebral artery ("MCA") in a brain of a patient. The MCA, as well as other vasculature in the brain or other relatively distal tissue sites (e.g., relative to the vascular access point), may be relatively difficult to reach with a catheter, due at least in part to the tortuous pathway (e.g., comprising relatively sharp twists or turns) through the vasculature to reach these tissue sites. Catheter body 12 may be structurally configured to be relatively flexible, pushable, and relatively kink- and buckle-resistant, so that it may resist buckling when a pushing force is applied to a relatively proximal section of the catheter to advance the catheter body distally through vasculature, and so that it may resist kinking when traversing around a tight turn in the vasculature. Kinking or buckling of catheter body 12 may hinder a clinician's efforts to push the catheter body distally, e.g., past a turn.

As discussed in further detail below, one structural characteristic that may contribute to at least the flexibility of catheter body 12 is the flexible distal section of the inner liner. The flexibility of the distal section may be at least in part due to one or more cuts (e.g., voids) defined in a liner wall of the distal section. The pattern of cuts may be selected to achieve the desired level of structural integrity (e.g., stiffness, tensile strength, and the like), while increasing flexibility of the distal section of the inner liner. The one or more cuts in a distal section of the inner liner may improve the navigability of catheter body 12 through vasculature of a patient.

In some examples, an outer diameter of catheter body 12 may be the same along the length of catheter body 12. In other examples, an outer diameter of catheter body 12 may taper from a first outer diameter at a proximal portion of catheter body 12 to a second outer diameter at a distal portion of catheter body 12, the second outer diameter being smaller than the first outer diameter. In some examples, the taper may be continuous along the length of catheter body 12, such that an outer surface of catheter body 12 defines a smooth transition between different diameter portions. In other examples, catheter body may define discrete step-downs in outer diameter to define the taper. The size of the discrete step-downs in diameter may be selected to reduce the number of edges that may catch on anatomical features within the vasculature as catheter body 12 is advanced through vasculature. A larger diameter proximal portion of catheter body 12 may provide better proximal support for catheter body 12, which may help increase the pushability of catheter body 12. In addition, a smaller diameter distal section may increase the navigability of catheter body 12 through tortuous vasculature. Thus, by reducing the outer diameter of catheter body 12 at distal section, which leads catheter body 12 through vasculature, catheter body 12 may better traverse through tortuous vasculature while still maintaining a relatively high level of proximal pushability.

In some examples, the outer diameter(s) of catheter body 12 is in a range of about 3 French to about 10 French, such as about 3 French to about 6 French. The measurement term French, abbreviated Fr or F, is three times the diameter of a device as measured in mm. Thus, a 6 French diameter is about 2 mm.

The proximal and distal sections of catheter body 12 may each have any suitable length. The working length of catheter body 12 may be measured from distal end 14B of hub 14 to distal end 12B of catheter body 12. In some examples, the length of the proximal section that extends from distal end 14B of hub 14 in the direction towards distal end 12B is about 38.16 inches (about 96.93 cm), and the distal section has a length of about 11.1 inches (about 30 cm). In some examples, the distal section has a length of about 10 cm to about 40 cm. In other examples, the distal section has a length of about 5 cm to about 35 cm, such as about 5 cm to about 10 cm. However, in other examples, the proximal and distal sections may have different lengths.

The diameter of inner lumen 26 (as measured in a direction perpendicular to a longitudinal axis 16 of catheter body 12) may vary based on the one or more procedures with which catheter 10 may be used. In some examples, the diameter of inner lumen 26 (shown in FIG. 2) of catheter body 12, also referred to herein as an inner diameter ("ID") of catheter body 12, may be substantially constant from proximal end 12A to distal end 12B. In an example, the inner diameter may be about 1.524 mm (about 0.060 inches) or larger. In other examples, the inner diameter may not be constant. For example, the inner diameter of catheter body 12 may taper from a first inner diameter at a proximal section that includes proximal end 12A to a second inner diameter at a distal section that includes distal end 12B, the second inner diameter being smaller than the first inner diameter. For example, an inner diameter of catheter body 12 may taper from a first inner diameter of about 0.0685 inches (about 1.74 mm) to a second inner diameter of about to 0.0605 inches (about 1.54 mm). The inner diameter may, for example, gradually taper in the direction along longitudinal axis 16, where the taper can be linear, curved, continuous or discontinuous; e.g., the inner diameter of catheter body 12 may step-down from the first inner diameter to the second inner diameter in discrete steps.

Catheter body 12 can be relatively thin-walled, such that it defines a relatively large inner diameter for a given outer diameter, which may further contribute to the flexibility and kink-resistance of catheter body 12. The wall thickness of catheter body 12 may be the difference between the outer diameter of catheter body 12 and the inner diameter of catheter body 12, as defined by inner lumen 26. The wall thickness of catheter body 12 may also be referred to as the thickness of the elongate body, such as $T_{CB}$ in FIG. 4.

In some examples, catheter body 12 may be formed from two or more discrete and separate longitudinally extending segments that are mechanically connected to each other, e.g., at axial butt joints. In other examples, catheter body 12 may be substantially continuous along a length of catheter body 12. For example, the inner liner of catheter body 12 may continuously extend from proximal end 12A to distal end 12B of catheter body 12, and a structural support member may span at least part of catheter body 12. A substantially continuous catheter body 12 may be better configured to better distribute forces in a longitudinal direction (in a direction along longitudinal axis 16) and rotational direction (rotation about longitudinal axis 16) compared to a catheter body including two or more longitudinally extending segments that are mechanically connected to each other. Thus, the substantially continuous construction of catheter body 12 may contribute to the ability of body 12 to transfer axial pushing forces from the proximal portion of catheter body 12 to the distal section, as well transfer rotational forces (if any) applied from the proximal portion of catheter body 12 to the distal portion of catheter body 12.

While in some examples, catheter body 12 includes an outer jacket formed of two or more longitudinally extending segments that are in an abutting relationship, due to the continuous inner liner and, in some examples, the structural support member that extends along a majority of the length of catheter body 12, catheter body 12 may still better distribute forces and flexibility compared to a catheter body including two or more longitudinal sections that are mechanically connected to each other. In some examples, the outer jacket is formed of a single segment. The inner liner or structural support member that extends through at least a part of the proximal section and at least part of distal portion of catheter body 12 may provide sufficient continuity to catheter body 12 to provide it with the desired force distribution characteristics for facilitating pushing of catheter body 12 to relatively distal tissue sites (e.g., distal vascular sites), and for facilitating rotational movement of catheter body 12.

In some examples, at least a portion of an outer surface of catheter body 12 includes one or more coatings, such as, but not limited to, an anti-thrombogenic coating, which may help reduce the formation of thrombi in vitro, an anti-microbial coating, or a lubricating coating. The lubricating coating may be configured to reduce static friction or kinetic friction between catheter body 12 and tissue of the patient as catheter body 12 is advanced through the vasculature. In addition, or instead, in some examples, the lubricating coating may be configured to reduce static or kinetic friction between catheter body 12 and another catheter through which catheter body 12 may be inserted. The lubricating coating can be, for example, a hydrophilic coating. In some examples, the entire working length of catheter body 12 (from distal section 14B of hub 14 to distal end 12B) is coated with the hydrophilic coating. In other examples, only a portion of the working length of catheter body 12 coated with the hydrophilic coating. This may provide a length of catheter body 12 distal to distal end 14B of hub 14 with which the clinician may grip catheter body 12, e.g., to rotate catheter body 12, pull catheter body 12 when removing catheter body 12 from the patient, or push catheter body 12 through vasculature.

FIG. 2 is a conceptual cross-sectional view of a part of a distal portion of catheter body 12 including distal end 12B, where the cross-section is taken through a center of catheter body 12 and along longitudinal axis 16 of catheter body 12. In some examples, catheter body 12 may be a tubular body, such that the cross-section shown in FIG. 2 illustrates one half of the tubular body. Catheter body 12 includes inner liner 18, which comprises liner wall 19 defining a plurality of cuts 20. In addition, the depicted catheter body 12 includes outer jacket 24, and support member 28. Inner liner 18 may define lumen 26, which extends from distal opening 13 at distal end 12B of catheter body 12 to proximal end 12A.

Lumen 26 may be sized to receive a medical device (e.g., another catheter, a guide member, an embolic protection device, a stent, a thrombectomy device, or any combination thereof), a therapeutic agent, or the like. At least the inner surface of inner liner 18 defining inner lumen 26 may be lubricious in some examples to facilitate the introduction and passage of a device, a therapeutic agent, or the like, through lumen 26. For example, the material from which the entire inner liner 18 is formed may be lubricious. In addition to, or instead of, being formed from a lubricious material, in some examples, an inner surface of inner liner 18 is coated with a lubricious coating.

Examples of materials from which inner liner 18 may be formed include, but are not limited to, PTFE, expanded PTFE (ePTFE, e.g., unidirectional ePTFE or bi-directional ePTFE), a fluoropolymer, perfluoroalkyoxy alkane (PFA), fluorinated ethylene propylene (FEP), or any combination thereof. A unidirectional ePTFE may be stretched in one of the longitudinal or radial directions, and a bi-directional ePTFE may be stretched in both the longitudinal and radial directions. Other examples of materials from which inner liner 18 may be formed include, but are not limited to, Low Density Polyethylene (LDPE) (e.g., about 42 D), a PTFE having a durometer of about 60 D, High Density Polyethylene (HDPE), or any combination thereof. Some such polyolefin materials may have similar coefficients of friction as PTFE, and may be conducive to processing.

Inner liner 18 includes proximal section 18A and distal section 18B. Distal section 18B includes a distal end of inner liner 18, which in the example shown in FIG. 2 is co-extensive with distal end 12B of catheter body 12. In other examples, the distal end of inner liner 18 may be proximal to distal end 12B of catheter body 12 or may extend distal to outer jacket 24. Distal section 18B may have any suitable length. In some examples, distal section 18B is about 5% to about 50% of a total length of inner liner 18, such as about 10% to about 40%, about 5% to about 25%, or about 10% to about 25% of the total length of inner liner 18. In some examples, distal section 18B has a length of about 5 cm to about 40 cm, such as about 5 cm to about 35 cm, or about 5 cm to about 10 cm. In some of these examples, inner liner 18 has a total length of about 132 cm.

Proximal section 18A includes a proximal end of inner liner 18, which may be co-extensive with distal end 12B of catheter body 12. In other examples, the proximal end of inner liner 18 may be proximal to proximal end 12B of catheter body 12 or may be distal to proximal end 12B. Proximal section 18A and distal section 18B may have different lengths in some examples, e.g., proximal section 18A may be longer than distal section 18B or proximal section 18A may be shorter than distal section 18B. In other examples, proximal section 18A and distal section 18B may substantially equal (e.g., equal or nearly equal) lengths.

In some examples, inner liner 18 consists essentially of proximal section 18A and distal section 18B. For example, proximal section 18A and distal section 18B may together extend the entire length of inner liner 18, as measured along longitudinal axis 16. In these examples, proximal section 18A may end where distal section 18B begins. In some examples, proximal section 18A and distal section 18B may be formed as separate structures, and then attached together at a butt joint or another suitable joint.

In other examples, proximal section 18A and distal section 18B may have a unitary body construction, e.g., may be formed as one body, such that liner wall 19 is continuous along the entire length of inner liner 18, such that inner liner 18 is a single, seamless tubular body. A seamless inner liner 18 may, for example, be devoid of any seams (e.g., the seam formed from joining two separate tubular bodies together at an axial location along longitudinal axis 16), such that the seamless inner liner 18 is a unitary body, rather than multiple, discrete bodies that are separately formed and subsequently connected together. A seamless inner liner 18 may be easier to slide over another device, e.g., a guide member, compared to a catheter formed from two or more longitudinal sections that are mechanically connected to each other because the seamless inner liner may define a smoother inner lumen 26. In contrast, joints between sections of an inner liner that are formed from two or more longitudinal sections may define surface protrusions or other irregularities along inner lumen 26 which may interfere with the passage of devices through inner lumen 26. In addition, a seamless inner liner 18 may help distribute pushing and rotational forces along the length of catheter body 12. Thus, the seamless inner liner 18 may help contribute to the pushability of catheter body 12.

In some examples, a thickness of liner wall 19 of inner liner 18 is substantially constant along a length of inner liner 18. In other examples, the thickness of liner wall 19 varies along a length of inner liner 18. For example, the thickness of liner wall 19 may decrease toward the distal end (e.g., the thickness of liner wall 19 may decrease from the proximal end to the distal end of inner liner 18, or may decrease from a proximal end of distal section 18B to a distal end of distal section 18B). For example, the thickness of liner wall 19 may decrease from about 0.33 millimeters (mm) at the proximal end of inner liner 18 to about 0.0127 mm (about 0.0005 inches) at the distal end of inner liner 18. However, other wall thicknesses may be used in other examples, and may depend on the particular procedure for which catheter 10 is used.

In the example of FIG. 2, liner wall 19 in distal section 18B of inner liner 18 defines a plurality of cuts 20. In other examples, liner wall 19 in distal section 18B may define only one cut, e.g., a helical cut or another cut configuration that extends along a length of distal section 18B. Although not shown in FIG. 2, in some examples, liner wall 19 in proximal section 18A of inner liner 18 may also define one or more cuts. However, in other examples, liner wall in proximal section 18A does not define any cuts. Regardless of whether proximal section 18A includes one or more cuts, distal section 18B of inner liner 18 may be more flexible than proximal section 18A, e.g., due to the presence and/or pattern of the one or more cuts 20, due to the material from which distal section 18B is formed, or any combination thereof.

In the example of FIG. 2, cuts 20 extend only partially through liner wall 19, and do not extend through an entire thickness of liner wall 19 (measured in a direction perpendicular to longitudinal axis 16 of catheter body 12, which may also be a longitudinal axis of inner liner 18). The depth of the partial cut 20 may be described as a percentage of the thickness of liner wall 19 or as a unit of length (e.g., millimeters). In some examples, the depth of a partial cut 20 may be about 20% to about 80% of the thickness of liner wall 19, such as about 50% to about 75% of the thickness of liner wall 19. In contrast, a through-cut 20 may extend through 100% of the thickness of liner wall 19.

In examples in which cuts 20 include a plurality of partial cuts, each partial cut may have a substantially similar depth or at least two of the partial cuts may have different depths. For example, each of the partial cuts may have the same depth as measured as a unit length. As another example, the unit length of the depths of the partial cuts may be different, but the depth as measured as a percentage of the thickness of liner wall 19 may be the same. If inner liner 18 is stretched during a manufacturing process, then a partial cut at a more distal portion of inner liner 18 may have a smaller depth in millimeters than a more proximal cut; however, the percentage of thickness of the depth of the two cuts may be substantially the same (e.g., equal or within 5% of each other)

In some examples in which cuts 20 are partial cuts, cuts 20 extend from an outer surface of liner wall 19 toward lumen 26, where the outer surface may be the surface closest to outer jacket 24 or other outer layer or surface of catheter body 12. In these examples, the inner surface of inner liner 18 defining lumen 26 may be relatively smooth, which may help facilitate the passage of medical devices through lumen 26. For example, a guide member may not catch on a cut 20 as it is being traversed through inner lumen 26 from proximal end 12A of catheter body 12 towards the distal end 12B. In other examples, cuts 20 may extend from an inner surface of liner wall 19, which defines lumen 26, towards the outer surface. In some of these examples, the cuts can be configured to minimize interference with a medical device being traversed through lumen 26. For example, an angular orientation of the cuts relative to an axis that runs orthogonal to longitudinal axis 16 may be selected to minimize the possibility that a guide member will catch on the cut.

Although inner liner 18 defining a plurality of cuts 20 is primarily described herein, in some examples, inner liner 18 may define only one cut, which may extend along a length (e.g., 5 cm to about 30 cm, such as about 5 cm to about 15 cm) of distal section 18B. For example, the single cut may be helically shaped and wrap around a perimeter of inner liner 18.

Cuts 20 may be positioned along any suitable length of distal section 18B. For example, a distal-most cut 20 may be proximal to distal end 12B of catheter body 12, as shown in FIG. 2. In some examples, the distal-most cut 20 (or, in the case of a helical cut, a distal end of the helical cut) may be relatively close to distal end 12B, such as about 0.2 mm to about 30 mm (e.g. about 0.254 mm (about 0.010 inches) to about 5 mm) from distal end 12B. A proximal-most cut 20 (or, in the case of a helical cut, a proximal end of the helical cut) may be, for example, about 5 cm to about 35 cm (e.g., about 6.6 cm to about 33 cm) from distal end 12B.

The one or more cuts 20 are configured to increase a bending flexibility of inner liner 18 and catheter body 12, e.g., such that distal end 12B may move relative to proximal end 12A or relative to an intermediate portion of catheter body 12. To facilitate this, the one or more cuts 20 may have any suitable arrangement relative to inner liner 18 and to each other if more than one cut 20 is defined in liner wall 19. In the example of FIG. 2, cuts 20 may be in the pattern shown in FIG. 13 or may have another pattern. In examples in which multiple cuts 20 are defined in liner wall 19, inner liner 18 can include any suitable number of cuts. In the example of FIG. 2, eight cuts 20 are shown on one side of longitudinal axis 16, and eight cuts 20 are shown on the other side of longitudinal axis 16. However, FIG. 2 may also illustrate an example in which inner liner 18 includes eight cuts that extend on side of longitudinal axis 16. In other examples, however, inner liner 18 may have another number and/or arrangement of cuts 20.

In some examples, each of the cuts 20 has the same configuration, such as the same shape and size. A size of a cut 20 may be defined by a depth, a length, and a width of the cut, which may be used to determine a volume of the cut. The width of a cut 20 may be measured in a direction along longitudinal axis 16. The depth may be measured in a direction perpendicular to longitudinal axis 16 or, in the case of a cut having a depth oriented at a non-perpendicular angle relative to longitudinal axis 16 in another direction that starts from the outer inner surface of liner wall 19 and towards or away from, respectively, inner lumen 26. The length of the cut measured from one end of the cut to the other end. In other examples, one cut 20 may have different configurations from at least one other cut 20. In some examples, a cut 20 may be oblong shaped, such that a major axis of the oblong shape extends in a direction substantially perpendicular to longitudinal axis 16. An oblong shaped cut may include, for example, an elongated rectangle, an elongated oval, ellipse, or the like.

Cuts 20 may define a pattern (also referred to herein as a cut pattern). The pattern may be symmetrical or asymmetrical. For example, cuts 20 may be symmetrically arranged relative to longitudinal axis 16, e.g., may have radial symmetry. Other types of symmetric patterns may be used for cuts 20, such as, but not limited to, reflection, rotational, glide reflection, or helical symmetry. In some examples, inner liner 18 may define a symmetrical cut pattern along one portion of distal section 18B and an asymmetrical cut pattern along a different portion of distal section 18B.

In some examples, inner liner 18 may include only one cut that winds helically around inner liner 18. The helical cut may define a helix having a pitch of about 1 mm to about 5 mm between adjacent turns of the cut, although a helical cut having other configurations may be used in other examples. In other examples, the pattern may be defined by multiple cuts in a repeated arrangement along a length of inner liner 18. For example, multiple sets of cuts may be positioned along the length of inner liner 18, each set including one or more cuts positioned around a perimeter (e.g., a circumference) of inner liner 18. In some examples, each set of cuts may be offset from an adjacent set circumferentially and/or longitudinally. Examples cut patterns are described with respect to FIGS. 13-17.

In some examples, each cut 20 does not overlap with any other cut 20. In other examples, at least one cut 20 overlaps with another cut 20. For example, a cut pattern may include a double helix shape, such as a first helical partial cut rotating counterclockwise along a length of the distal section, and a second helical partial cut rotating clockwise along the same length of the distal section, such that the two cuts overlap at multiple points along the distal section. As another example, two non-helical cuts may overlap to form an "X" shape.

Cuts 20 may have a density, which may be the number of cuts 20 per unit length of inner liner 18 (the length being measured in a direction along longitudinal axis 16). If inner liner 18 defines a single cut 20, e.g., a single helically shaped cut, then the density of the cut may correspond to a number of turns the cut makes around an outer (or inner) circumference of inner liner 18 per a length of inner liner 18.

In some examples, the density of cuts 20 may be the same along a length of inner liner 18. In other examples, however, the density of cuts 20 may vary along the length of inner liner 18. For example, the density of cuts 20 may increase in the distal direction, such that there are more cuts 20 near a distal end of inner liner 18 than near the proximal end. In these examples, for an inner liner 18 that is otherwise the same, a distal portion of distal section 18B of inner liner 18 may have a greater bending flexibility than a more proximal portion of distal section 18B. In another example, the density of cuts 20 may decrease in the distal direction, such that there are fewer cuts 20 near a distal end of inner liner 18 than near the proximal end. In these examples, for an inner liner 18 that is otherwise the same, a distal portion of distal section 18B of inner liner 18 may be stiffer than a more proximal portion of distal section 18B.

In some examples, the density of cuts 20 on inner liner 18 may be about 4% to about 30% (e.g., such as about 5% to about 25%, about 11% to about 19%, or about 14%). That is, about 4% to about 30% of inner liner 18 may be cut. The percentage of inner liner 18 that is cut may be, for example, a percentage of an area of an outer surface of inner liner 18.

Inner liner 18 defining cuts 20 may be formed using any suitable technique. In some examples, cuts 20 may be etched, laser cut, or mechanically cut via a blade, router, abrasion disk, or the like into a tubular body or other material from which inner liner 18 is formed. In other examples, inner liner 18 may be formed by winding a ribbon of an inner liner material (e.g., PTFE) around a beading. As another example, inner liner 18 may be formed using an additive manufacturing process (also referred to as a three-dimensional printing technique in some examples). Cuts 20 may then be defined during the additive manufacturing.

Support member 28 is configured to increase the structural integrity of catheter body 12 while allowing catheter body 12 to remain relatively flexible. For example, support member 28 may be configured to help catheter body 12 substantially maintain its cross-sectional shape or at least help prevent catheter body 12 from buckling or kinking as it is navigated through tortuous anatomy. In some examples, catheter body 12 may include another layer, such as a support layer (not shown in FIG. 2) that adheres support member 28 to one or both inner liner 18 or outer jacket 24. Support member 28, together with inner liner 18, and outer jacket 24, may help distribute both pushing and rotational forces along a length of catheter body 12, which may help prevent kinking of catheter body 12 upon rotation of body 12 or help prevent buckling of body 12 upon application of a pushing force to body 12. As a result, a clinician may apply pushing forces, rotational forces, or both, to the proximal portion of catheter body 12, and such forces may cause a distal portion of catheter body 12 to advance distally, rotate, or both, respectively.

In the example of FIG. 2, support member 28 extends along only a portion of a length of catheter body 12. For example, a proximal end of support member 28 may be positioned distal to distal end 14B of hub 14 (or of strain relief 11) and a distal end of support member 28 may be positioned at distal end 12B of catheter 12 or proximal to distal end 12B. In other examples, a proximal end of structural support member 28 may be positioned proximal to distal end 14B of hub 14 and a distal end of member 28 be positioned at distal end 12B of catheter 12 or proximal to distal end 12B. In some examples, support member 28 may be fully or partially co-extensive with distal section 18B of inner liner 18. In some these examples, support member 28 may be arranged relative to inner liner 18 so that support member 28 does not sit in or otherwise cover a cut 20. In other examples, support member 28 may not be coextensive with distal section 18B, i.e., may be proximal to the entire distal section 18B. Further, in other examples, catheter body 12 may not include support member 28.

In some examples, support member 28 includes a generally tubular braided structure, a coil member defining a plurality of turns, e.g., in the shape of a helix, or a combination of a braided structure and a coil member. Thus, although examples of the disclosure describe support member 28 as a coil, in some other examples, the catheter bodies described herein include a braided structure instead of a coil or a braided structure in addition to a coil. For example, a proximal portion of support member 28 may include a braided structure and a distal portion of structural support member 28 may include a coil member. Support member 28 can be made from any suitable material, such as, but not limited to, a metal (e.g., a nickel titanium alloy (Nitinol) or stainless steel), a polymer, a fiber, or any combination thereof.

Support member 28 may be coupled, adhered, or mechanically connected to at least a portion of an outer surface of inner liner 18, such as via a support layer. The support layer may be a thermoplastic material or a thermoset material, such as a thermoset polymer or a thermoset adhesive. In some cases, the material forming the support layer may have elastic properties, such that there may be a tendency for the support layer to return to a resting position. In some examples, the support layer is positioned between the entire length of support member 28 and inner liner 18. In other examples, the support layer is only positioned between a part of the length of support member 28 and inner liner 18.

Outer jacket 24 is positioned radially outward of inner liner 18 and support member 28, and may be positioned around or covers at least a part or all of both inner liner 18 and support member 28. The support member 28 is positioned between inner liner 18 and outer jacket 24 in at least some portions of catheter body 12. In some examples, outer jacket 24 defines the outer surface of catheter body 12. Although a coating or another material may be applied over the outer surface of outer jacket 24, outer jacket 24 may still substantially define shape and size of the outer surface of catheter body 12. Outer jacket 24, together with inner liner 18 and support member 28, may be configured to define catheter body 12 having the desired flexibility, kink resistance, torque responsiveness, structural integrity, and pushability characteristics.

Outer jacket 24 may have stiffness characteristics that contribute to the desired stiffness profile of catheter body 12. For example, outer jacket 24 may be formed to have a stiffness that decreases from a proximal end 12A of catheter body 12 to distal end 12B. For example, outer jacket 24 may be formed from two or more different materials that enable outer jacket 24 to exhibit the desired stiffness characteristics. In some examples, outer jacket 24 may define a durometer gradient along longitudinal axis 16. For example, outer jacket 24 may be defined by a plurality of tubular segments extending from proximal end 12A to distal end 12B wherein each tubular segment defines a different durometer. The durometer gradient of outer jacket 24 may be selected to help provide catheter body 12 with the desired flexibility characteristics. For example, in some examples in which catheter body 12 increases in flexibility from proximal end 12A towards distal end 12B, the durometer gradient of outer jacket 24 may decrease in a direction from proximal end 12A towards distal end 12B. In some examples, the durometer gradient of outer jacket 24 may decrease in a direction from proximal end 12A towards distal end 12B and then increase just proximate of distal end 12B to provide an increased flexibility about distal portion 17B while also increasing the hardness about distal opening 13 to resist geometric deformation when distal opening 13 (FIG. 1) of catheter body 12 is engaged with a guide member, which may help support the navigation of catheter body 12 through vasculature. In some examples, the durometer of outer jacket 24 may be from about 25 D to about 75 D. For example, outer jacket 24 may define a durometer gradient from proximal end 12A towards distal end 12B that generally decreases from about 75 D to about 25 D, with a distal segment defining distal opening 13 having a durometer greater than 25 D (e.g., 55 D).

Example materials that may be used to form outer jacket 24 include, but are not limited to, polymers, such as a polyether block amide (e.g., PEBAX®, commercially available from Arkema Group of Colombes, France), an aliphatic polyamide (e.g., Grilamid®, commercially available from EMS-Chemie of Sumter, S.C.), another thermoplastic elastomer, polyurethanes, or other thermoplastic material, or combinations thereof.

In some examples, at least a portion of an outer surface of outer jacket 24 includes one or more coatings, such as, but not limited to, an anti-thrombogenic coating, which may help reduce the formation of thrombi in vitro, an antimicrobial coating, and/or a lubricating coating.

Figure 3:
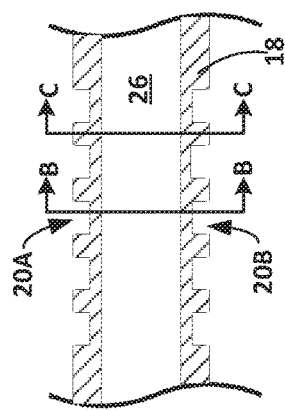
FIG. 3 is a conceptual cross-sectional view of a part of an example inner liner of the catheter body of FIG. 1, where the cross-section is taken through a center of the inner liner and along a longitudinal axis of the inner liner.

FIG. 3 is a conceptual cross-sectional view of a part of inner liner 18, where the cross-section is taken through a center of inner liner 18 and along longitudinal axis 16. In the example shown in FIG. 3, cuts 20 defined in liner wall 19 of inner liner 18 include cuts 20A and 20B. Cuts 20A, 20B are partial cuts that only extend partially through a thickness of liner wall 19. In some examples, cuts 20A, 20B are separate cuts that are axially aligned along longitudinal axis 16 and circumferentially spaced from each other by a part of liner wall 19. In other examples, cuts 20A, 20B may be part of a common cut and may be continuous with each other, e.g., may extend partially or fully around an outer perimeter of inner liner 18.

Figure 6:
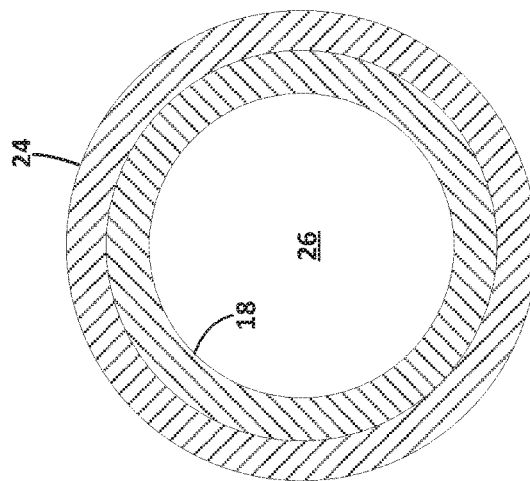
FIG. 6 is a conceptual cross-sectional view of the catheter body of FIG. 1, such as taken along line C-C in FIGS. 1 and 3.
Figure 5:
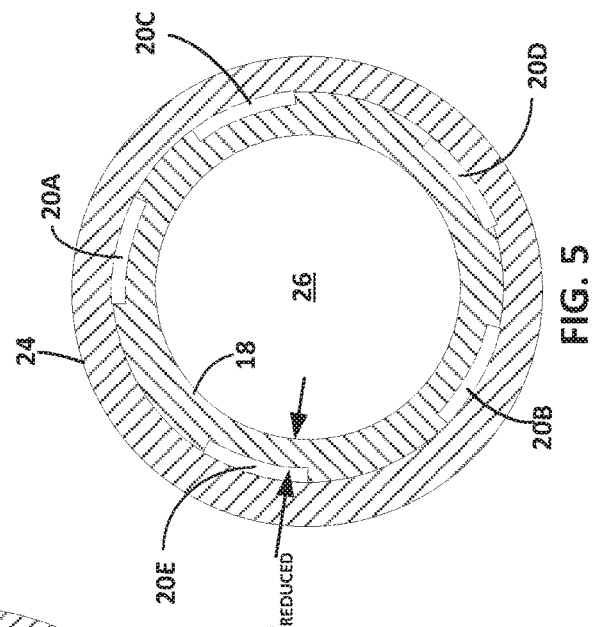
FIG. 5 is a conceptual cross-sectional view of the catheter body of FIG. 1, such as taken along line B-B in FIGS. 1 and 3.
Figure 4:
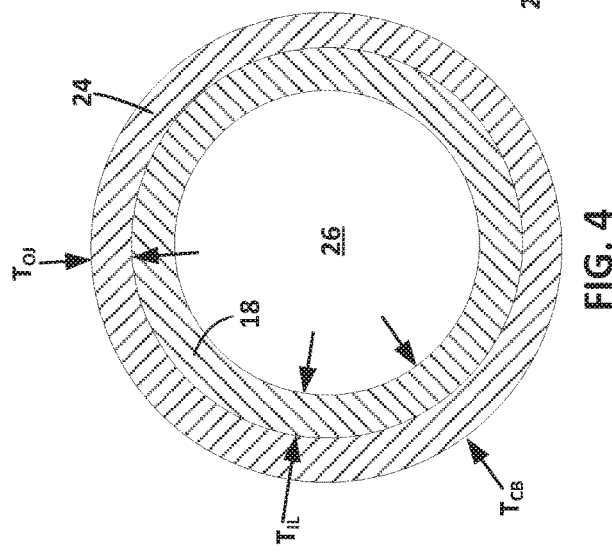
FIG. 4 is a conceptual cross-sectional view of the catheter body of FIG. 1, such as taken along line A-A in FIG. 1.

FIGS. 4-6 illustrate respective conceptual cross-sectional views of catheter body 12. FIG. 4 is a conceptual cross-sectional view of catheter body 12 of FIG. 1 taken along line A-A in FIG. 1. In an example, line A-A is positioned in proximal section 18A of inner liner 18. FIG. 4 illustrates a thickness of outer jacket 24 ($T_{OJ}$), a thickness of inner liner 18 ($T_{IL}$), and the thickness of catheter body 12 ($T_{CB}$). In the example shown in FIG. 4, proximal section 18A of inner liner 18 does not define any cuts through a thickness $T_{IL}$ of inner liner 18 (which may also be a thickness of liner wall 19).

In the example shown in FIG. 4, the total thickness $T_{CB}$ of catheter body 12 is equal to the thickness $T_{IL}$ of inner liner 18 plus the thickness $T_{OJ}$ of outer jacket 24. In some examples in which catheter body 12 includes support member 28, support member 28 may also be seen in the cross-sectional view shown FIG. 4, positioned between inner liner 18 and outer jacket 24. In some of these examples, support member 28 may also contribute to the total thickness $T_{CB}$ of catheter body 12. In other examples, however, support member 28 may be embedded in one or both of inner liner 18 or outer jacket 24, and, therefore, may not contribute to the total thickness $T_{CB}$ of catheter body 12.

As discussed above, cuts 20 defined by distal section 18B of inner liner 18 may have any suitable arrangement relative to each other. In some examples, a plurality of cuts 20 are aligned along longitudinal axis 16 and distributed around a circumference of inner liner 18. An example of such an arrangement is shown in FIG. 5, which is a conceptual cross-sectional view of catheter body 12 taken along line B-B in FIGS. 1 and 3. FIG. 5 illustrates a cross-section of a portion of distal section 18B of inner liner 18 that defines some of the cuts 20. In the example shown in FIG. 5, cuts 20 defined in liner wall 19 of inner liner 18 include cuts 20A-20E, which are aligned along longitudinal axis 16, and, therefore shown in the cross-sectional view of FIG. 5. Cuts 20A-20E are also circumferentially distributed around an outer perimeter of inner liner 18. As shown in FIGS. 3 and 5, cuts 20A and 20B may be at least partially diametrically opposed to one another. However, as discussed with respect to FIGS. 13-18, inner liner 18 may have a different arrangement of cuts 20 in other examples.

FIG. 6 is a conceptual cross-sectional view of catheter body 12 taken along line C-C in FIGS. 1 and 3, and illustrates a cross-section of a portion of distal section 18B of inner liner 18 that does not include any cuts 20. In an example, thickness $T_{IL}$ of inner liner 18 is substantially uniform between the proximal and distal ends of inner liner 18. This may mean, for example, that although cuts 20 are present in distal section 18B of inner liner 18, a thickness of liner wall 19 at a position where there are no cuts 20 may be substantially the same as a thickness of liner wall 19 in proximal section 12A. In an example, this may mean that inner liner 18 has substantially similar cross-sections at lines A-A and C-C (FIGS. 1 and 3), even though the thickness of liner wall 19 is different at line B-B (e.g., FIGS. 1 and 3). In other examples, a thickness of inner liner 18 may not be uniform along longitudinal axis 16 (e.g., in the case of a tapering inner liner 18).

As shown in FIGS. 5 and 6, in the portion of distal section 18B of inner liner 18 that defines one or more cuts 20, inner liner 18 has a recued thickness $T_{REDUCED}$ compared to thickness $T_{IL}$. As a result of this reduced thickness $T_{REDUCED}$, an overall stiffness of distal section 18B of inner liner 18 may be reduced, thereby allowing distal section 18B to flex (e.g., bend) more readily in response to a given external force compared to an inner liner having a constant thickness $T_{IL}$.

Inner liner 18 may define a substantially constant (e.g., identical or nearly identical) inner diameter along the entire length of inner liner 18, while in other examples, inner liner 18 may define different inner diameters. For example, proximal section 18A of inner liner 18 may define a first inner diameter and distal section 18B may define a second inner diameter, the second inner diameter being smaller than the first inner diameter. For example, inner liner 18 may taper continuously from the first inner diameter to the second inner diameter, or may define one or more step-downs in inner diameter along the length of inner liner 18.

Figure 7:
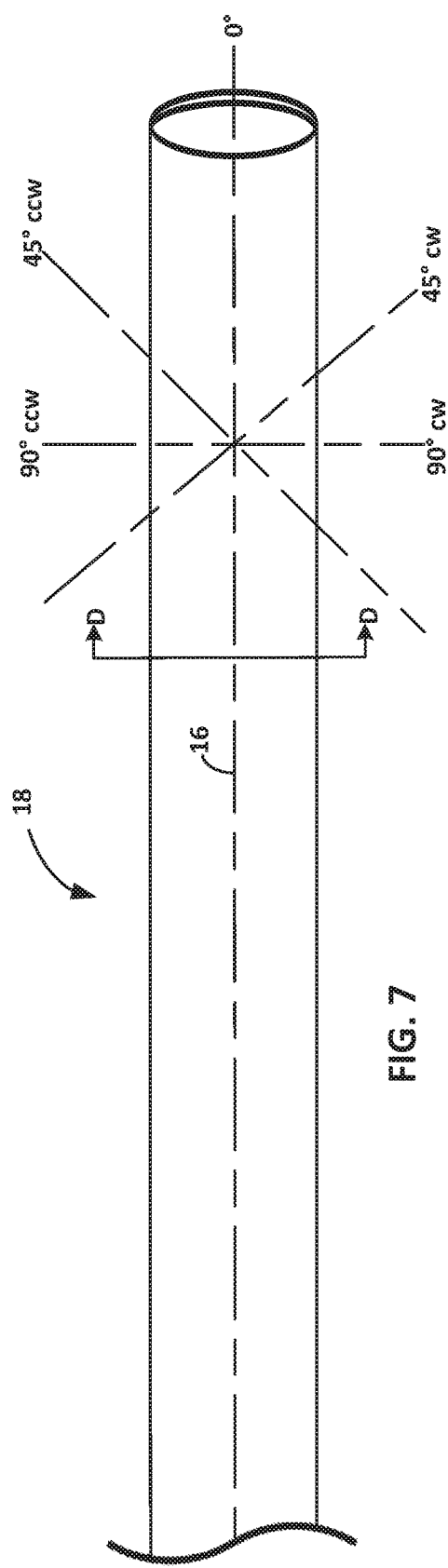
FIG. 7 is a conceptual illustration of an example inner liner of a catheter body and illustrates examples of angles of cuts, where the angles are measured relative to a longitudinal axis of the inner liner.
Figure 8:
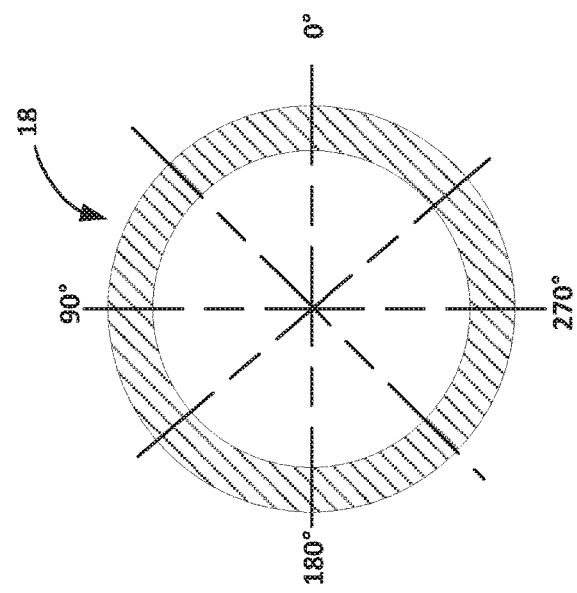
FIG. 8 is a conceptual cross-sectional view of the inner liner of FIG. 7 taken along line D-D in FIG. 7.

Cuts 20 defined in liner wall 19 of inner liner 18 may have different angular orientations relative to longitudinal axis 16 of catheter body 12 (or of inner liner 18). FIGS. 7 and 8 are conceptual illustrations of inner liner 18 and provide frameworks for describing the angular orientations of cuts 20 relative to longitudinal axis 16. FIG. 7 illustrates a framework for describing the angular orientations of cuts 20 in a plane that extends in a longitudinal direction, e.g., in a direction along longitudinal axis 16. In the framework shown in FIG. 7, the angular orientation of longitudinal axis 16 corresponds to 0 degrees. A longitudinal angle that is orthogonal to longitudinal axis 16 is 90 degrees, either clockwise or counterclockwise, as shown in FIG. 7.

In some examples, cuts 20 define arc segments that are elongated in a direction relative to longitudinal axis 16, such that the ends of the cut are not axially aligned along longitudinal axis 16, but, rather, may be axially displaced and, in some examples, circumferentially displaced from each other. For example, one or more cuts 20 may be elongated in a direction that includes angles from about 45 degrees to about 90 degrees relative to longitudinal axis 16. As another example, one or more cuts 20 may be elongated in a direction that includes angles less than 45 degrees relative to longitudinal axis 16. Other examples, cuts 20 may be disposed around inner liner 18, such that a cut has an arc segment that is perpendicular to longitudinal axis 16, e.g., cut 20A of FIG. 5. In some examples, at least one of cuts 20 may be elongated in a direction substantially perpendicular to longitudinal axis 16 (e.g., from about 85 degrees to about 95 degrees relative to longitudinal axis 16 such as 88 degrees to 92 degrees relative to longitudinal axis 16, or 90 degrees relative to longitudinal axis 16). In some examples, at least one of cuts 20 may be elongated in a direction substantially parallel to longitudinal axis 16 (e.g., about −5 degrees to about 5 degrees relative to longitudinal axis 16 such as −2 degrees to 2 degrees relative to longitudinal axis 16, or 0 degrees relative to longitudinal axis 16).

In some examples, a cut 20 may be oriented such that a maximum depth of the cut is along an axis that is oriented about 90 degrees in the angular framework shown in FIG. 7. In other examples, a cut may be oriented such that a maximum depth of the cut is along an axis that is oriented less than 90 degrees relative to longitudinal axis 16, e.g., about 15 degrees to about 89 degrees in either the clockwise (cw) direction or the counterclockwise (ccw) direction.

FIG. 8 is a conceptual cross-sectional view of inner liner 18 of FIG. 7, where the cross-section is taken in a direction perpendicular to longitudinal axis 16. The angles illustrated in the example of FIG. 8 are shown around a circumference of inner liner 18, and illustrate a framework for describing the circumferential position of, e.g., a cut 20 or a plurality of cuts relative to each other, as well as an orientation of the cut in a depth direction. In some examples, a cut 20 may be extend less than 360 degrees around a circumference of inner liner 18, such as, but not limited to, about 30 degrees to about 180 degrees. In these examples, the cut 20 may not be elongated relative to longitudinal axis 16 or may be elongated relative to longitudinal axis 16 (e.g., the ends of the cut may be longitudinally offset from each other). When a cut is not relative to longitudinal axis 16, the cut may have a 90-degree orientation (as shown in FIG. 7) relative to longitudinal axis 16.

In other examples a cut may extend about 360 degrees around a circumference of the inner liner, but due to the elongation of the cut, the cut does not divide inner liner 18 into physically separate portions.

In some examples, at least some cuts 20 may be arranged with radial symmetry, such that the at least some cuts 20 are equidistant from one another around a circumference of inner liner 18. However, in other examples, cuts 20 may be radially asymmetrical. When cuts 20 are described as being circumferentially aligned in some examples, the cuts 20 may have the same angular position, a framework for describing the angular position being shown in FIG. 8.

FIGS. 9-18 illustrate other example configurations of cuts defining an inner liner of catheter body 12. Each of the inner liners shown in FIGS. 9-18 may be similar to inner liner 18, but have a different cut configuration or pattern.

FIGS. 2,3, and 5 illustrate an example inner liner 18 defining cuts 20 that extend only partially through a thickness of liner wall 19. As discussed above, in other examples, inner liner 18 may define through-cuts instead of or in addition to partial cuts. For example, an example inner liner may comprise only partial cuts or only through-cuts. As another example, an example inner liner may comprise both partial cuts and through-cuts, such that a percentage of the cuts are partial cuts, and another percentage of the cuts are through-cuts. For example, an example inner liner 18 may comprise about 50% through-cuts and about 50% partial cuts, or any other percentage combination.

Figure 9:
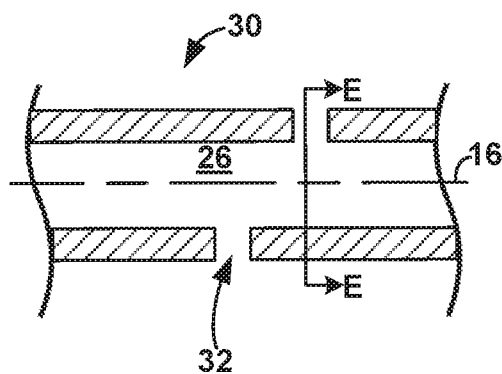
FIG. 9 is a conceptual cross-sectional view of a part of an example inner liner of a catheter body, where the cross-section is taken through a center of the inner liner and along a longitudinal axis of the inner liner.
Figure 10:
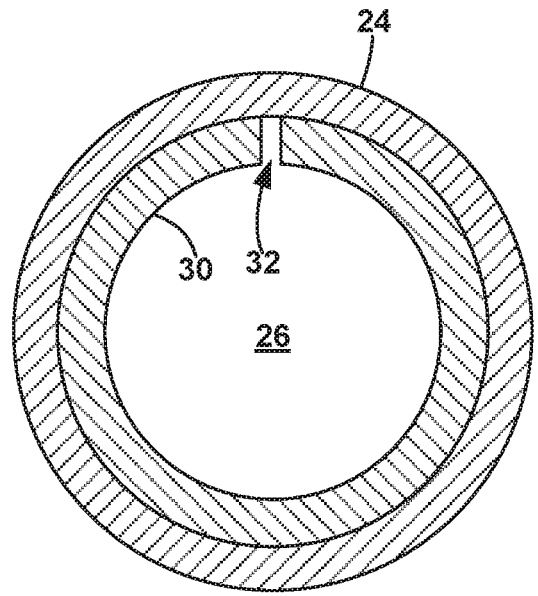
FIG. 10 is a conceptual cross-sectional view of a catheter body including the inner liner of FIG. 9, where the cross-section is taken along line E-E in FIG. 9.

FIGS. 9 and 10 illustrate an example inner liner 30 that defines a plurality of through-cuts 32. FIG. 9 is a conceptual cross-sectional view of a part of an example inner liner 32 of a catheter body, where the cross-section is taken through a center of inner liner 32 and along a longitudinal axis 16 of inner liner 30. FIG. 10 is a conceptual cross-sectional view of an example of a catheter body that includes inner liner 30 and outer jacket 24, where the cross-section of inner liner 30 is taken through a through-cut 32 along line E-E in FIG. 9. As shown in FIGS. 9 and 10, through-cut 32 extends through a thickness of a liner wall of inner liner 30 from inner lumen 26 defined by inner liner 30 to an outer surface of inner liner 30.

Figure 11:
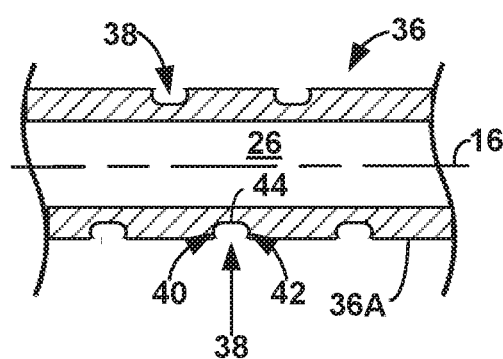
FIG. 11 is a conceptual cross-sectional view of a part of an example inner liner of a catheter body, where the cross-section is taken through a center of the inner liner and along a longitudinal axis of the inner liner.
Figure 12:
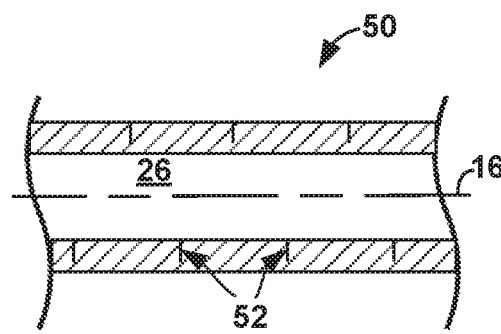
FIG. 12 is a conceptual cross-sectional view of a part of an example inner liner of a catheter body, where the cross-section is taken through a center of the inner liner and along a longitudinal axis of the inner liner.

As discussed above, cuts 20 defined in inner liner 18 may have any suitable configuration. For example, FIG. 2 illustrates example cuts 20 that have a rectangular shape in a cross-section taken along longitudinal axis 16. FIGS. 11 and 12 illustrate other example cut configurations.

FIG. 11 is a conceptual cross-sectional view of a part of an example of inner liner 36, where the cross-section is taken through a center of inner liner 36 and along a longitudinal axis 16 of inner liner 36. A liner wall of inner liner 36 defines a plurality of cuts 38, which are each a partial cut having a curved shape in cross-section. For example, walls 40, 42 of cut 38 are concave and a bottom surface 44 of cut 38 is relatively flat. In some examples, cut 38 has a smooth inner surface. A depth of cut 38 may be measured, for example, from an outer surface 36A of inner liner 36 to bottom surface 44.

FIG. 12 is a conceptual cross-sectional view of a part of an example of an inner liner 50 of a catheter body, where the cross-section is taken through a center of the inner liner and along a longitudinal axis 16 of inner liner 50. In some examples, the plurality of cuts defined in a liner wall of inner liner 50 include one or more slits 52. A slit may be a cut in inner liner 50 where no material is removed. Slits 52 may be partial slits that only extend partially through a thickness of a liner wall of inner liner 50. In these examples, slits 52 may extend from an inner surface of inner liner 50 towards the outer surface or may extend from the outer surface of inner liner 50 towards inner lumen 26. In other examples, slits 52 may be through-slits that extend through the entire thickness of the liner wall. Slits 52 may have any suitable arrangement and configuration, including those described with reference to cuts above and below.

Cuts 20 defined in distal section 18B of inner liner 18 of a catheter body 12 may be sized, shaped, and arranged to increase a bending flexibility of distal section 18B and a corresponding distal portion of catheter body 12. In some examples, each cut of the plurality of cuts 20 are substantially the same size and shape (e.g., designed to be the same size and shape, but due to manufacturing variances, may slightly differ in size and/or shape). The shape of the cut may refer to characteristics such as a shape of the ends of the cut (e.g., rounded or squared ends), the direction of elongation relative to longitudinal axis 16, or cross-sectional profile. In addition to the pattern of cuts 20, the arrangement of cuts may also refer to a density of cuts 20 along inner liner 18, which may be a number of cuts per unit length of inner liner 18 (measured along longitudinal axis 16).

Figure 13:
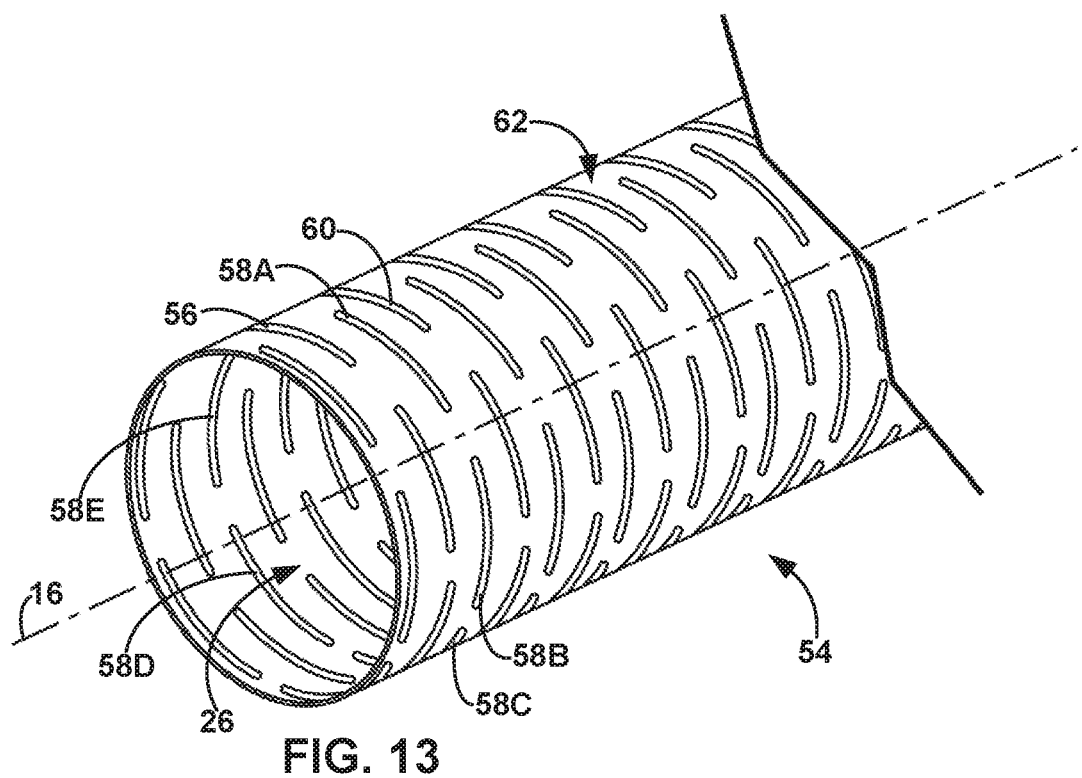
FIG. 13 is a perspective view of a distal section of an example inner liner of a catheter body.

FIGS. 13-17 illustrate example cut patterns, sizes, shapes, and densities of cuts defined in liner wall of the inner liner. FIG. 13 is a perspective view of an example inner liner 54 that defines plurality of through-cuts, e.g., 56, 58A-58E, 60, which each fully extend through a thickness of liner wall 62 of inner liner 54 and expose inner lumen 26. In other examples, one or more of the cuts 56, 58A-58E, 60 may be partial cuts, which do not fully penetrate through the thickness of liner wall 54. In the example of FIG. 13, the cuts defined by inner liner 54 are arranged as a plurality of sets of cuts that are axially spaced from one other (in a direction along longitudinal axis 16). Each set of cuts may include a plurality of axially aligned cuts axially aligned with each other (aligned longitudinal axis 16) and circumferentially offset from each other. For example, a first set of cuts may include cut 56 and the cuts shown in FIG. 13 as being axially aligned with cut 56, a second set of cuts may include cuts 58A-58E, and a third set of cuts may include cut 60 and the cuts shown in FIG. 13 as being axially aligned with cut 60.

In the example of FIG. 13, the sets of cuts are substantially similar (in number of cuts, size of cuts, shape of cuts, and the like), but the cuts of each set may be longitudinally and circumferentially offset from the cuts of an immediately adjacent set. For example, cuts of the first set of cuts are longitudinally and circumferentially offset from the cuts of the second set of cuts. As shown in FIG. 13, cut 56 of the first set is not circumferentially aligned with any of cuts 58A-58E of the second set, but, rather, is offset from cuts 58A and 58E by an angle between about 5 degrees and about 90 degrees. In the example shown in FIG. 13, the cuts of adjacent sets are circumferentially offset from one another by about 30 degrees. Thus, in the example shown in FIG. 13, adjacent sets of cuts are circumferentially rotated 30 degrees relative to each other. Other circumferential offset values may be used. In some examples, the cuts of adjacent sets are circumferentially offset from one another by about 5 degrees and about 90 degrees (e.g., about 15 degrees or about 45 degrees).

In the example shown in FIG. 13, every other set of cuts is substantially aligned circumferentially. For example, cut 56 of the first set may be circumferentially aligned (but axially offset) from cut 60 of the third set.

Circumferentially offsetting adjacent sets of cuts may help improve the structural integrity of inner liner 54, e.g., may make inner liner 54 less likely to kink in response to a given bending force compared to inner liner 54 including adjacent sets of cuts that are circumferentially aligned. In addition, offsetting adjacent sets of cuts may help improve the radial distribution of forces in inner liner 54 when external pressure is applied to inner liner 54, due at least in part to the more omnidirectional flexural stiffness. The more the cuts (e.g., 56 or 60) are circumferentially aligned, the more unidirectional the flexural stiffness.

Each set of cuts may have any suitable number of cuts, such as, but not limited to the five shown in FIG. 13, or fewer than five or greater than five. Cuts of the same set may share a circumferential axis. Other configurations of sets of cuts may be used. For example, the sets of cuts shown in FIG. 13 may be circumferentially aligned, such that cuts of each set are directly adjacent to aligned with a cut of an adjacent set.

Figure 14:
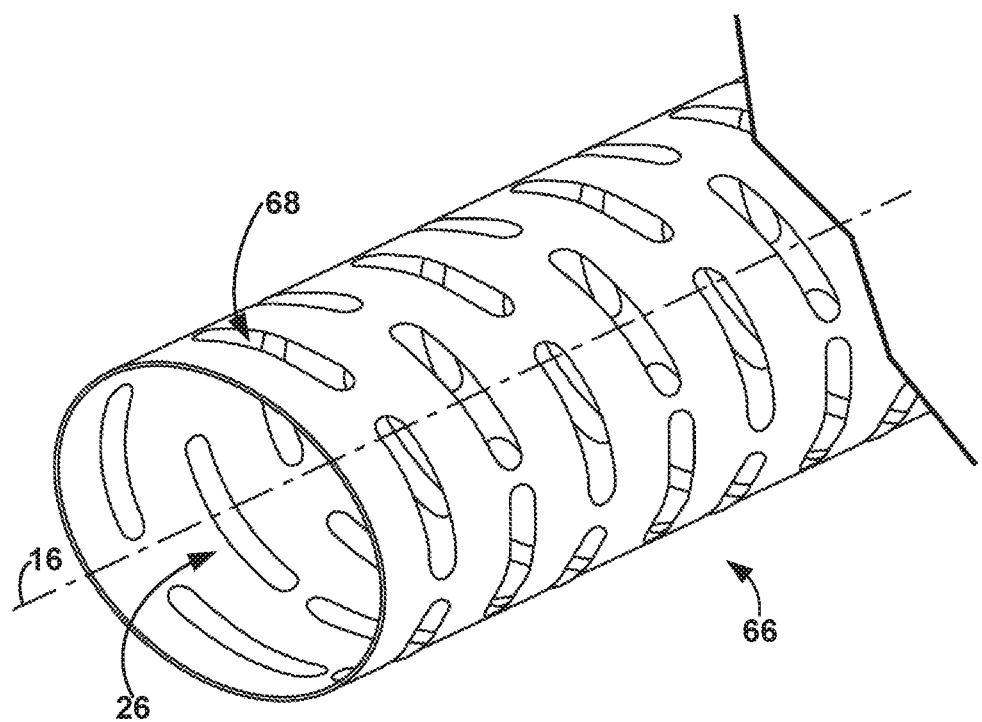
FIG. 14 is a perspective view of a distal section of another example inner liner of a catheter body.

FIG. 14 is a perspective view of inner liner 66 defining a cut pattern that includes a plurality of cuts 68. The cut pattern in the example of FIG. 14 may be similar to the cut pattern in FIG. 13, and may include multiple sets of cuts, where each set is displaced from an adjacent set both longitudinally and circumferentially. Some characteristics of cuts 68 in the example of FIG. 14 may be different than the cuts of the example of FIG. 13. For example, the width of cuts 68 may be greater than the width of cuts shown in FIG. 13, and the length of cuts 68 may be smaller than the length of cuts shown in FIG. 13. As another example, a cut density of cuts 68 may be less than a cut density of cuts shown in FIG. 13. However, due to the wider width of cuts 68, the overall percentage of inner liner 66 shown in FIG. 14 that is cut may be the same as or greater than the overall percentage of inner liner 54 shown in FIG. 13 that is cut.

FIG. 15 is a perspective view of inner liner 70 and illustrates an example cut pattern that includes a plurality of cuts, which include a first set of cuts 72 and a second set of cuts 74. In the example shown in FIG. 15, the sets of cuts 72, 74 are on opposite sides of a median plane 75 which bisects inner liner 70 along longitudinal axis 16. In some examples, the sets of cuts 72, 74 on either side of median plane 75 may mirror each other, such that there is mirror symmetry in cuts 72, 74. In other examples, the sets of cuts 72, 74 on either side of median plane 55 may have other symmetrical arrangements. The cuts of the sets of cuts 72, 74 may be through-cuts or partial cuts. In other examples, one or both sets of cuts 72, 74 includes both through-cuts and partial-cuts. The symmetry in the cuts may extend to the type of cut, and not just the location of cuts.

FIG. 16 is a perspective view of an example inner liner 76 and illustrates an example of a cut pattern in inner liner 76. The cut pattern shown in FIG. 16 includes a plurality of through-cuts cuts 78, including through-cuts 78A, 78B, and 78C, which each fully extend through a thickness of liner wall 79 and expose inner lumen 26. In other examples, one or more of the cuts 78 may be partial cuts, which do not fully penetrate through the thickness of liner wall 79. In the example of FIG. 16, cuts 78 have both radial and longitudinal components. For example, the ends of each of the cuts 78 are both longitudinally and circumferentially offset from each other, such that each of the cuts 78 extends both longitudinally and circumferentially around inner liner 76. In contrast, the ends of cut 58 (FIG. 13) are longitudinally aligned, but circumferentially offset from each other. Angular orientation of cuts 78 include angles of about 10 degrees to about 80 degrees (using the framework shown in FIG. 7) relative to longitudinal axis 16, in either clockwise or counterclockwise directions. In an example, the angular orientation of cuts 78 is about 30 degrees relative to longitudinal axis 16.

Cuts 78 may each extend around any suitable percentage of the outer circumference of inner liner 76. For example, ends of a cut 78 may be longitudinally offset, but circumferentially aligned, such that the cut 78 extends around 360 degrees of the outer circumference of inner liner 76. As another example, ends of a cut 78 may be both longitudinally and circumferentially offset, such that the cut 78 extends around less than 360 degrees of the outer circumference of inner liner 76.

In some examples, at least some cuts 38 may be partially or fully circumferentially aligned with another cut. For example, cuts 56, 60 shown in FIG. 13 are longitudinally offset from each other, but fully circumferentially aligned (e.g., such that the ends of the cuts 56, 60 have the same circumferential position relative to an outer circumference of inner liner 18, as described using the framework shown in FIG. 8). In contrast, cuts 78A, 78B are partially circumferentially offset from each other, but also partially circumferentially aligned. An end portion of cut may, for example, circumferentially overlap with an end portion of adjacent cut 78B.

In the pattern shown in FIG. 16, adjacent cuts 78 (e.g., cuts 78A, 78B or cuts 78B, 78C) may be circumferentially offset from one another by about 5 degrees to about 90 degrees (such as about 30 degrees to about 60 degrees or about 45 degrees, using the framework shown in FIG. 8). In other examples, however, adjacent cuts 38 may be fully circumferentially aligned.

In the example of FIG. 16, cuts 78 are substantially similar (e.g., similar or nearly similar sizes and shapes) to each other. In other examples, however, at least some cuts 78 may have a different configuration than each other. For example, at least one cut 78 may have a different length, width, or depth than another cut 78.

In addition, in the example cut patterns shown in FIGS. 2, 13, 14, 15, and 16, the cuts (generally referred to herein as "cuts 20") of inner liner 18 are substantially evenly (e.g., evenly or nearly evenly) spaced from each other along longitudinal axis 16. In these examples, inner liner 18 may have a uniform density of cuts 20. A uniform density of cuts 20 may provide a distal section 18B of inner liner 18 that exhibits substantially uniform bending flexibility and tensile strength. In other examples of inner liner 18, however, inner liner 18 may define a cut pattern that includes an increasing or decreasing density of cuts 20 along longitudinal axis 16, towards a distal end of inner liner 18. To achieve an increasing density of cuts 20, cuts 20 adjacent to each other in the longitudinal direction may be spaced closer to each other, such that there are more cuts 20 per unit length of inner liner 18. To achieve a decreasing density of cuts 20, cuts 20 adjacent to each other in the longitudinal direction may be spaced further part, such that there are fewer cuts 20 per unit length of inner liner 18.

Any of the cuts in inner liner 18 described herein may also have a uniform width and thickness along its length. In other examples, a cut in inner liner 18 described herein may also have a varying width and/or thickness along its length. For example, in FIG. 16, one of the cuts 38 may be deeper along a medial portion than at the end portions, the greater depth resulting in greater bending flexibility of inner liner 76 at the medial portion of the cut 78.

Figure 17:
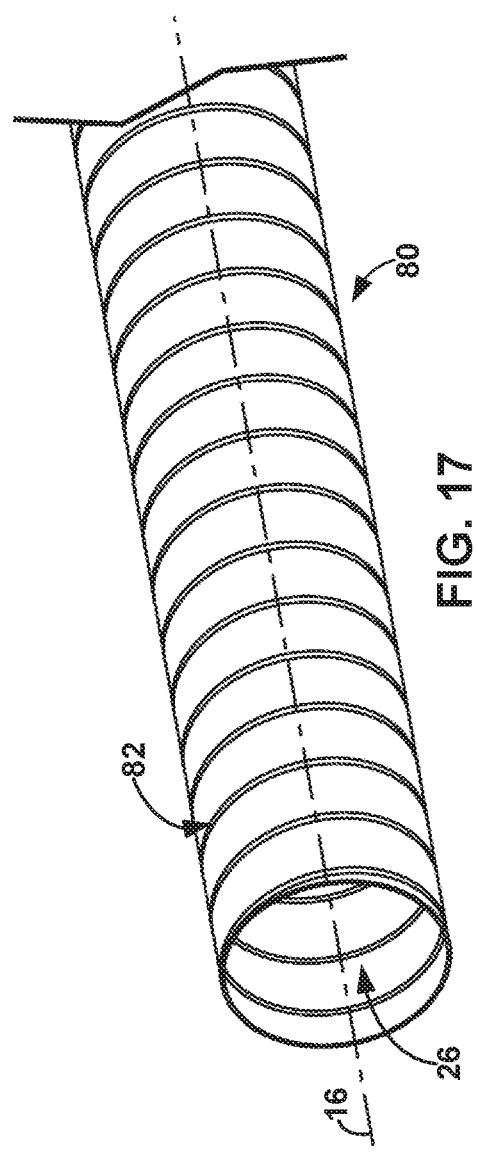
FIG. 17 is a perspective view of a distal section of another example inner liner of a catheter body.

As discussed above, in some examples, inner liner 18 defines a plurality of cuts 20 (e.g., as shown in FIGS. 13 to 16), while in other examples, inner liner 18 defines only one cut (a single cut). The single cut may include both circumferential and longitudinal components in some examples. FIG. 17 is a perspective view of an example inner liner 80 that includes a single cut 82 that has both circumferential and longitudinal components. For example, single cut 82 may have a helical configuration that spirals around the circumference of inner liner 80 about longitudinal axis 16. Cut 82 may be a partial cut and/or a through-cut. In some examples, cut 80 defines a helix having a pitch of about 1 mm to about 5 mm between adjacent turns of the cut, although a helical cut defining outer pitches may be used in other examples.

Cuts, as described herein, may comprise multiple portions, such that a first portion includes a through-cut, and such that a second portion includes a partial cut. For example, cut 82 in the example of FIG. 17 may comprise multiple portions, where some portions of cut 82 are through-cut portions and other portions of cut 82 are partial cut portions. These portions may have any suitable arrangement relative to each other. For example, the through-cut portions of cut 82 may be positioned between two partial cut portions of cut 82. As another example, a partial cut portion of cut 82 may be positioned between two through-cut portions of cut 82.

Figure 18:
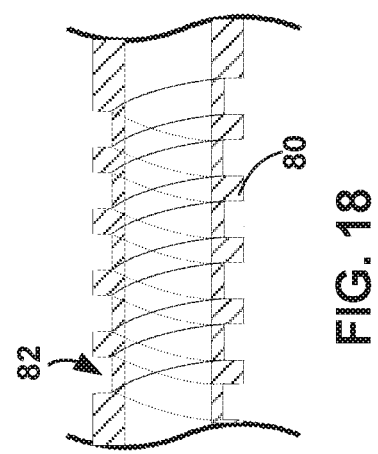
FIG. 18 is a conceptual cross-sectional view of a part of an example inner liner of a catheter body, where the cross-section is taken through a center of the inner liner and along a longitudinal axis of the inner liner.

FIG. 18 is a conceptual cross-sectional view of a part of an example of inner liner 80 of a catheter body, where the cross-section is taken through a center of the inner liner and along a longitudinal axis 16 of inner liner 80. In an example, helical cut 82 wraps around inner liner 80. Although illustrated with relatively evenly spaced cycles around inner liner 80, in some examples, such a helical pattern may include an increasing density of cycles in the direction of longitudinal axis 16.

Figure 19:
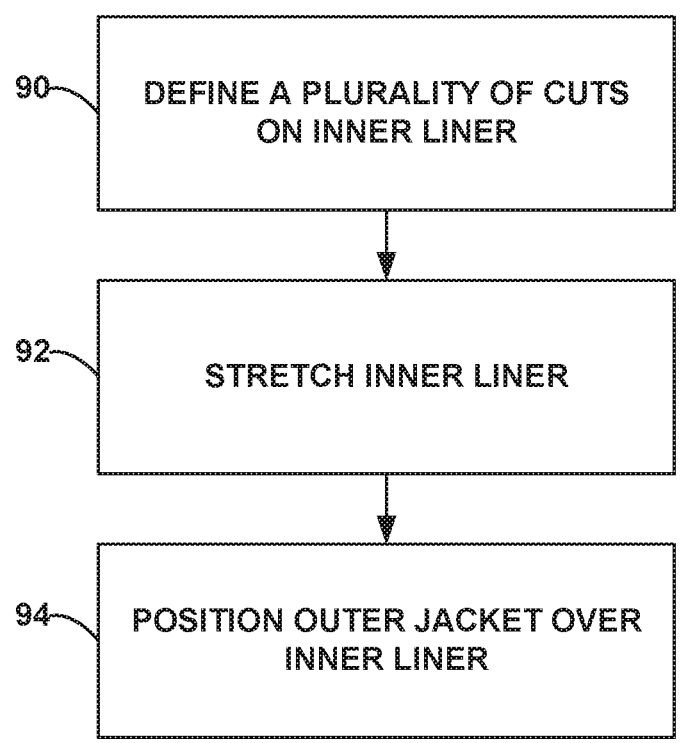
FIG. 19 is a flow diagram of an example method of forming a catheter.

The catheter bodies described herein may be formed using any suitable technique. FIG. 19 is a flow diagram of an example method of forming catheter body 12. In accordance with the technique shown in FIG. 19, a plurality of cuts 20 are defined in inner liner 18 (90). Any suitable device may be used to form inner liner 18 defining a plurality of cuts 20. In some examples, the cuts are formed into a tubular body. For example, a mechanical cutting tool, such as a rotating blade, may be used to define cuts 20 in the tubular body. As another example, a laser cutter may be used to define cuts 20 in the tubular body to form inner liner 18.

In some examples in which a laser cutter is used, inner liner 18 may be positioned over a mandrel. In some examples, inner liner 18 is a unitary, seamless body, and may be positioned over the mandrel by at least inserting the mandrel through an end of inner liner 18. A laser (e.g., a carbon dioxide laser cutter) may then be used to define cuts 20. One or more parameters of the laser may be adjusted in order to modify the characteristics (e.g., a shape, depth, width, and/or length) of the cuts being defined in inner liner 18. For example, a power of the laser, a focal point of the laser, an ultraviolet wavelength of the laser, or a speed of movement of the laser relative to inner liner 18 may be modified in order to achieve the desired cut size and pattern. A width of a cut 20 may be a function of a focal width of the laser. In addition, a depth of the cut may be a function of the ultraviolet wavelength or speed of the laser relative to inner liner 18. Further, a suitable depth of the cut may be achieved by repeated laser rastering, such as over the same path.

In other examples, inner liner 18 defining a plurality of cuts 20 is formed using additive manufacturing techniques, such as three-dimensional printing. As another example, inner liner 18 may be formed by depositing an inner liner material (e.g., PTFE) over a mask, where the mask shape defines the location and size of the cuts 20. The material may be deposited using any suitable technique, such as, but not limited to, spray deposition, dip coating, or the like. In some examples, the material is deposited in layers (e.g., 1-2 microns thick) and liner wall 19 is formed by building-up a plurality of layers.

In the example shown in FIG. 19, inner liner 18 is stretched (92). Inner liner 18 may be stretched at different points in time relative to the definition of a plurality of cuts in inner liner 18 (90). For example, stretching inner liner 18 can occur prior to defining a plurality of cuts in inner liner 18 (90) or after defining a plurality of cuts in inner liner 18 (90). In some examples, the defining of cuts (90) and stretching (92) may be performed more than once, such as first stretching the inner liner, then defining a plurality of cuts, then stretching the inner liner again. In some examples, inner liner 18 is formed by ram extruding the liner material (e.g., PTFE) or film casting the liner material, and cuts 20 may be made in inner liner 18 after inner liner 18 is extruded but before the inner liner is stretched. Stretching inner liner 18 may help increase an axial strength of inner liner and thin liner wall 19, e.g., from about 0.033 mm to about 0.020 mm. In other examples, cuts 20 may be made in inner liner 18 after inner liner 18 is extruded and stretched. After being stretched, the length of inner liner 18 may be longer and the liner wall thickness may be smaller. A thinner liner wall 19 may result in a softer and more flexible inner liner 18. In other examples of the technique shown in FIG. 19, inner liner 18 may not be stretched.

If catheter body 12 includes support member 28, support member 28 may be positioned around inner liner 18 before or after being stretched. As shown in FIG. 19, outer jacket 24 may be positioned around inner liner 18 (and support member 28 if present) (94). Outer jacket 24 may be connected to inner liner 18 using any suitable technique. For example, outer jacket 24 may be heat shrunk around inner liner 18. A suitable technique for connecting outer jacket 24 to inner liner 18 may include, heating outer jacket 24 while outer jacket 24 is in heat shrink tubing enough to cause the material of outer jacket 24 to melt, then reflow the material of outer jacket 24. Other techniques may also be used to connect outer jacket 24 to inner liner 18.

Catheter 10 may be used for medical procedures. For example, a guidewire may be introduced into a patient. Catheter body 12 may be introduced in the patient over the guidewire. In an example, a medical device may be introduced into inner lumen 26 of catheter body 12. In an example, catheter 10 may be used for aspirating a thrombus. In an example, distal end 12B of catheter body 12 may be introduced into an intracranial blood vessel, and a thrombus may be removed from the blood vessel through inner lumen 26 of catheter body 12, such as via aspiration or using a thrombus retrieval device.

In some cases, catheter body 12 is advanced over an inner catheter having a smaller outer diameter than catheter body 12, rather than directly over a guidewire. The inner catheter may, for example, help fill the space between the guidewire and the outer surface of outer catheter body 12 to help minimize the ledge effect, which may occur when a distal tip of catheter body 12, particularly the portion of the edge of the tip that tracks along the outside of a curve formed by the body 12, engages with or tracks along a wall of vasculature as catheter body 12 is advanced over a guidewire through a curve in the vasculature. The ledge effect may, at least in part, be attributable to unopposed space between the guidewire and lumen 26 of catheter body 12. In some examples, catheter body 12 that includes inner liner 18 formed from PTFE may define opening 13 that is configured to resist geometric deformation may allow catheter body 12 to be guided through vasculature over a guidewire, without need for an inner catheter. Cuts 20 defined in inner liner 18 may help improve the navigability of the PTFE inner liner by increasing the bending flexibility of distal section 18B of inner liner 18. The elimination of an inner catheter may not only reduce costs associated with the medical procedure, but may also reduce the time required to reach the target tissue site as a step of guiding the inner catheter to the tissue site before guiding catheter 10 to the target tissue site may be eliminated.

The examples described herein may be combined in any permutation or combination.

Various aspects of the disclosure have been described. These and other aspects are within the scope of the following claims.

What is claimed is:

1. A catheter comprising:
   an elongated body including:
      an inner liner extending between a proximal end and a distal end, the inner liner comprising an inner surface that defines an inner lumen of the elongated body, wherein the inner liner includes a proximal section including the proximal end and a distal section including the distal end, wherein the distal section of the inner liner includes a liner wall defining a plurality of cuts, and wherein the inner liner is unitary; and
      an outer jacket positioned over the inner liner and fixed to the inner liner,
      wherein the outer jacket extends over the plurality of cuts, wherein each cut of the plurality of cuts forms a cavity radially bound by at least one of the inner liner or the outer jacket, and wherein the inner liner is formed from a more lubricous material than the outer jacket.

2. The catheter of claim 1, wherein at least one cut of the plurality of cuts is a through-cut that extends through a thickness of the liner wall to the inner lumen.

3. The catheter of claim 1, wherein at least one cut of the plurality of cuts is a partial cut, wherein the partial cut extends only partially through a thickness of the liner wall.

4. The catheter of claim 3, wherein the at least one cut extends from an outer surface of the liner wall and radially inward towards the inner lumen.

5. The catheter of claim 3, wherein the at least one cut extends through about 20% to about 80% of the thickness of the liner wall.

6. The catheter of claim 1, wherein at least one cut of the plurality of cuts is disposed in an arc around an outer surface of the inner liner.

7. The catheter of claim 1, wherein at least one cut of the plurality of cuts is elongated in a direction substantially perpendicular to a longitudinal axis of the inner liner.

8. The catheter of claim 1, wherein at least one cut of the plurality of cuts is oblong shaped, a major axis of the oblong shape extending in a direction substantially perpendicular to a longitudinal axis of the inner liner.

9. The catheter of claim 1, wherein each cut of the plurality of cuts is elongated in a direction that defines an angle from about 45 degrees to about 90 degrees relative to a longitudinal axis of the inner liner.

10. The catheter of claim 1, wherein at least one cut of the plurality of cuts is elongated in a direction substantially parallel to a longitudinal axis of the inner liner.

11. The catheter of claim 1, wherein the inner liner has a circular cross-section, and at least one cut of the plurality of cuts extends around only part of a circumference of the circular cross-section.

12. The catheter of claim 1, wherein a density of the plurality of cuts decreases in a proximal direction, wherein the density corresponds to a number of cuts per unit length of the inner liner.

13. The catheter of claim 1, wherein the plurality of cuts are symmetrically arranged relative to a longitudinal axis of the inner liner.

14. The catheter of claim 1, wherein the plurality of cuts are asymmetrically arranged relative to a longitudinal axis of the inner liner.

15. The catheter of claim 1, wherein a distal-most cut of the plurality of cuts is arranged between about 0.02 centimeters and about 30 centimeters from the distal end of the inner liner, and wherein a proximal-most cut of the plurality of cuts is about 5 centimeters to about 35 centimeters from the distal end of the inner liner.

16. The catheter of claim 1, wherein the elongated body extends along a longitudinal axis, wherein the inner liner comprises an inner liner portion and the outer jacket comprises an outer jacket portion longitudinally aligned with the inner liner portion, wherein the inner liner portion is formed from a first material having a first hardness and the outer jacket portion is formed from an outer liner material having a second hardness, the second hardness being greater than the first hardness.

17. The catheter of claim 1, wherein each cavity is radially sealed by the outer jacket.

18. A catheter comprising:
an elongated body including:
an inner liner extending between a proximal end and a distal end, the inner liner comprising an inner surface that defines an inner lumen of the elongated body, wherein the inner liner includes a proximal section including the proximal end and a distal section including the distal end, wherein the distal section of the inner liner includes a liner wall defining a helical cut, and wherein the inner liner is unitary; and
an outer jacket positioned over the inner liner and fixed to the inner liner,
wherein the outer jacket extends over the helical cut,
wherein the helical cut forms a cavity radially bound by at least one of the inner liner or the outer jacket, and
wherein the inner liner is formed from a more lubricous material than the outer jacket.

19. The catheter of claim 18, wherein the helical cut is a through-cut that extends through a thickness of the liner wall to the inner lumen.

20. The catheter of claim 18, wherein the helical cut is a partial cut extending only partially through a thickness of the liner wall.

21. The catheter of claim 18, a proximal end of the helical cut is about 5 centimeters to about 35 centimeters from the distal end of the inner liner.

22. The catheter of claim 18, wherein the cavity is radially sealed by the outer jacket.

* * * * *